United States Patent
Davis et al.

(10) Patent No.: US 10,132,493 B2
(45) Date of Patent: Nov. 20, 2018

(54) STEAM GENERATION APPARATUS AND ASSOCIATED CONTROL SYSTEM AND METHODS FOR PROVIDING DESIRED STEAM QUALITY

(71) Applicant: Skavis Corporation, Woodstock, GA (US)

(72) Inventors: Randall J. Davis, Woodstock, GA (US); Charles F. Noll, Jr., Woodstock, GA (US)

(73) Assignee: Skavis Corporation, Woodstock, GA (US)

( * ) Notice: Subject to any disclaimer, the term of this patent is extended or adjusted under 35 U.S.C. 154(b) by 152 days.

(21) Appl. No.: 15/078,411

(22) Filed: Mar. 23, 2016

(65) Prior Publication Data

US 2016/0202197 A1    Jul. 14, 2016

Related U.S. Application Data

(62) Division of application No. 14/030,667, filed on Sep. 18, 2013, now Pat. No. 9,383,095.

(51) Int. Cl.
*G06F 19/00*    (2018.01)
*F22B 35/16*    (2006.01)
(Continued)

(52) U.S. Cl.
CPC ............. *F22B 35/16* (2013.01); *F22B 15/00* (2013.01); *F22B 35/00* (2013.01); *F22B 37/38* (2013.01); *F22B 37/52* (2013.01); *F23N 1/022* (2013.01); *G01N 25/42* (2013.01); *G01N 25/60* (2013.01); *Y10T 137/0324* (2015.04); *Y10T 137/85986* (2015.04)

(58) Field of Classification Search
CPC .......... F22B 35/16; F22B 37/52; F22B 15/00; F22B 35/00; F22B 37/38; G01N 25/42; G01N 25/60; F23N 1/022; Y10T 137/85986; Y10T 137/0324
See application file for complete search history.

(56) References Cited

U.S. PATENT DOCUMENTS 2,688,942 A    9/1954    Bailey et al.
3,244,898 A    4/1966    Hickox
(Continued)

FOREIGN PATENT DOCUMENTS

WO    2015041660    3/2015

OTHER PUBLICATIONS

"Thermodynamics, Linear Interpolation", message board post and reply taken from www.physicsforums.com, Mar. 12, 2010.*
(Continued)

*Primary Examiner* — Michael D Masinick
(74) *Attorney, Agent, or Firm* — Taylor English Duma LLP

(57) ABSTRACT

The current disclosure relates to steam generation and supply apparati and associated control systems. Particularly, the current disclosure relates to such steam generation supply apparati and associated control systems that are used for enhanced oil recovery. Certain embodiments are provided including methods and associated control systems related to the startup as well as main steam pressure header control or maintenance of a desired steam quality for such steam generation systems during normal operation.

19 Claims, 24 Drawing Sheets

(51) Int. Cl.
| | |
|---|---|
| *F22B 37/38* | (2006.01) |
| *F22B 35/00* | (2006.01) |
| *F23N 1/02* | (2006.01) |
| *G01N 25/42* | (2006.01) |
| *G01N 25/60* | (2006.01) |
| *F22B 15/00* | (2006.01) |
| *F22B 37/52* | (2006.01) |

(56) References Cited

U.S. PATENT DOCUMENTS

| | | | |
|---|---|---|---|
| 3,415,232 A | 12/1968 | Garrett, Jr. | |
| 3,465,726 A | 9/1969 | Gerst | |
| 4,401,345 A | 8/1983 | Archibald | |
| 4,541,365 A | 9/1985 | Jennings et al. | |
| 4,679,947 A * | 7/1987 | Miller | G01N 9/002 374/42 |
| 4,712,006 A | 12/1987 | Zemel | |
| 4,860,827 A | 8/1989 | Lee | |
| 4,887,431 A | 12/1989 | Peet | |
| 4,888,953 A * | 12/1989 | Fukayama | F01K 13/02 60/646 |
| 4,903,769 A | 2/1990 | Hsueh | |
| 4,912,732 A | 3/1990 | Singh | |
| 4,914,705 A | 4/1990 | Nigawara | |
| 5,281,100 A | 1/1994 | Diederich | |
| 5,291,190 A | 3/1994 | Scarola et al. | |
| 5,309,487 A | 5/1994 | McDermott et al. | |
| 5,533,337 A | 7/1996 | Kusayama | |
| 5,619,433 A * | 4/1997 | Wang | G05B 17/02 703/18 |
| 5,772,403 A | 6/1998 | Allison et al. | |
| 5,790,420 A * | 8/1998 | Lang | F23N 5/003 700/287 |
| 5,797,357 A | 8/1998 | Kawachi et al. | |
| 6,655,322 B1 | 12/2003 | Godwin et al. | |
| 6,708,651 B1 | 3/2004 | Sun | |
| 8,097,128 B1 | 1/2012 | Sherry | |
| 8,839,746 B2 * | 9/2014 | Lelic | F22B 35/00 122/135.1 |
| 9,303,865 B2 | 4/2016 | Davis et al. | |
| 9,303,866 B2 | 4/2016 | Davis | |
| 9,310,070 B2 | 4/2016 | Davis | |
| 9,383,095 B2 | 7/2016 | Davis et al. | |
| 2003/0072403 A1 | 4/2003 | Dagard | |
| 2004/0194467 A1 | 10/2004 | Herzog et al. | |
| 2004/0221660 A1 * | 11/2004 | Dutton | G01F 1/74 73/861.354 |
| 2005/0279110 A1 | 12/2005 | Zeng | |
| 2006/0225422 A1 * | 10/2006 | Prentice, III | F23G 5/006 60/645 |
| 2007/0012556 A1 | 1/2007 | Lum | |
| 2009/0320828 A1 | 12/2009 | Koketsu et al. | |
| 2010/0312490 A1 | 12/2010 | Dooley | |
| 2011/0000281 A1 | 1/2011 | Deacon | |
| 2011/0100005 A1 | 5/2011 | Sampson et al. | |
| 2011/0162591 A1 * | 7/2011 | Fan | F23N 5/006 122/14.21 |
| 2011/0162593 A1 | 7/2011 | Miura | |
| 2011/0214858 A1 | 9/2011 | Castrogiovanni | |
| 2012/0160011 A1 | 6/2012 | Whittaker | |
| 2013/0133751 A1 | 5/2013 | Backi et al. | |
| 2013/0136435 A1 | 5/2013 | Graibus | |
| 2013/0161009 A1 | 6/2013 | Price | |
| 2013/0213279 A1 * | 8/2013 | Lelic | F22B 35/00 110/186 |
| 2014/0102382 A1 | 4/2014 | Kemp | |
| 2014/0195067 A1 * | 7/2014 | Abrol | G05D 9/12 700/301 |
| 2014/0311251 A1 | 10/2014 | Hutchinson | |
| 2015/0027384 A1 | 1/2015 | Akinaga et al. | |
| 2015/0075627 A1 | 3/2015 | Davis | |
| 2015/0075628 A1 | 3/2015 | Davis | |
| 2015/0075629 A1 | 3/2015 | Davis | |
| 2015/0075630 A1 | 3/2015 | Davis | |
| 2015/0198546 A1 | 7/2015 | Wang | |
| 2015/0275688 A1 | 10/2015 | Barenbrugge | |
| 2015/0276209 A1 | 10/2015 | Barenbrugge | |
| 2016/0116157 A1 * | 4/2016 | Agar | F22B 1/28 392/394 |

OTHER PUBLICATIONS

"Steam Tables: Properties of Saturated Superheated Steam"; 1967 ASME Steam Tables, 1967.*

Davis, Randall J.; Issue Notification for U.S. Appl. No. 14/030,666, filed Sep. 18, 2013, dated Mar. 23, 2016, 1 pg.

Davis, Randall J.; Notice of Allowance for U.S. Appl. No. 14/030,667, filed Sep. 18, 2013, dated Apr. 29, 2016, 9 pgs.

Davis, Randall J.; International Preliminary Report on Patentability for PCT Application No. PCT/US13/60788, filed Sep. 20, 2013, dated Mar. 31, 2016, 19 pgs.

Davis, Randall J.; Issue Notification for U.S. Appl. No. 14/030,618, filed Apr. 5, 2016, dated Mar. 16, 2016, 1 pg.

Davis, Randall J.; Notice of Allowance for U.S. Appl. No. 14/030,618, filed Sep. 18, 2013, dated Dec. 14, 2015, 17 pgs.

Davis, Randall J.; Supplemental Notice of Allowability for U.S. Appl. No. 14/030,618, filed Sep. 18, 2013, dated Feb. 17, 2016, 7 pgs.

Davis, Randall J.; U.S. Patent Application entitled: Steam Generation Apparatus and Associated Control System and Methods for Startup, having U.S. Appl. No. 14/030,618, filed Sep. 18, 2013, 63 pgs.

Davis, Randall J.; U.S. Divisional Application entitled: Steam Generation Apparatus and Associated Control System and Methods for Startup having U.S. Appl. No. 15/058,040, filed Mar. 1, 2016, 62 pgs.

Davis, Randall J.; Issue Notification for U.S. Appl. No. 14/030,656, filed Sep. 18, 2013, dated Mar. 16, 2016, 1 pg.

Davis, Randall J.; Notice of Allowance for U.S. Appl. No. 14/030,656, filed Sep. 18, 2013, dated Dec. 14, 2015, 18 pgs.

Davis, Randall J.; Supplemental Notice of Allowability for U.S. Appl. No. 14/030,656, filed Sep. 18, 2013, dated Feb. 17, 2016, 7 pgs.

Davis, Randall J.; U.S. Patent Application entitled: Steam Generation Apparatus and Associated Control System and Methods for Providing a Desired Injection Pressure, having U.S. Appl. No. 14/030,656, filed Sep. 18, 2013, 64 pgs.

Davis, Randall J.; U.S. Divisional Application entitled: Steam Generation Apparatus and Associated Control System and Methods for Providing a Desired Injection Pressure having U.S. Appl. No. 15/058,044, filed Mar. 1, 2016, 62 pgs.

Davis, Randall J.; Notice of Allowance for U.S. Appl. No. 14/030,666, filed Sep. 18, 2013, dated Dec. 11, 2015, 17 pgs.

Davis, Randall J.; Supplemental Notice of Allowability for U.S. Appl. No. 14/030,666, filed Sep. 18, 2013, dated Feb. 17, 2016, 7 pgs.

Davis, Randall J.; U.S. Patent Application entitled: Steam Generation Apparatus and Associated Control System and Methods for Providing Venting, having U.S. Appl. No. 14/030,666, filed Sep. 18, 2013, 64 pgs.

Davis, Randall J.; U.S. Divisional Application entitled: Steam Generation Apparatus and Associated Control System and Methods for Providing Venting having U.S. Appl. No. 15/058,048, filed Mar. 1, 2016, 62 pgs.

Davis, Randall J.; Non-Final Office Action for U.S. Appl. No. 14/030,667, filed Sep. 18, 2013, dated Dec. 14, 2015, 20 pgs.

Davis, Randall J.; U.S. Patent Application entitled: Steam Generation Apparatus and Associated Control System and Methods for Providing Desired Steam Quality, having U.S. Appl. No. 14/030,667, filed Sep. 18, 2013, 64 pgs.

Davis, Randall J.; International Search Report and Written Opinion for serial No. PCT/US13/60788, filed Sep. 20, 2013, dated Apr. 16, 2014, 22 pgs.

Davis, Randall J.; PCT application entitled: Steam Generation Apparatus and Associated Control System and Methods, having serial No. PCT/US13/60788, filed Sep. 20, 2013, 75 pgs.

(56) References Cited

OTHER PUBLICATIONS

Article entitled: "Main Steam Supply and Feedwater System", Training Centre/Centre de formation; Jan. 1996, 214 pgs.
Article entitled: "Secondary Pressure Drainer (SPD) Received/ Reservoir sizing", Fluid Control Institute Tech Sheet #SPD 2015, Oct. 26, 2007, 5 pgs.
Article Entitled: "steam Systems", CleaverBrooks, located at <http:// www.cleaverbrooks.com/Reference-center/Boiler-Basics/Steam-Systems.aspx.
Exxonmobile; Corporate Citizenship Report, 2013, 84 pgs.
Davis, Randall J.; Non-Final Office Action for U.S. Appl. No. 15/058,040, filed Mar. 1, 2016, dated Mar. 20, 2018, 31 pgs.
Davis, Randall J.; Non-Final Office Action for U.S. Appl. No. 15/058,044, filed Mar. 1, 2016, dated Jan. 25, 2018, 33 pgs.
Davis, Randall J.; Non-Final Office Action for U.S. Appl. No. 15/058,048, filed Mar. 1, 2016, dated Mar. 22, 2018, 35 pgs.
Davis, Randall J.; Supplemental Notice of Allowability for U.S. Appl. No. 14/030,667, filed Sep. 18, 2013, dated Jun. 3, 2016, 7 pgs.
Davis, Randall J.; Notice of Allowance for U.S. Appl. No. 15/058,040, filed Mar. 1, 2016, dated Aug. 9, 2018, 22 pgs.
Davis, Randall J.; Notice of Allowance for U.S. Appl. No. 15/058,044, filed Mar. 1, 2016, dated Sep. 13, 2018, 5 pgs.

* cited by examiner

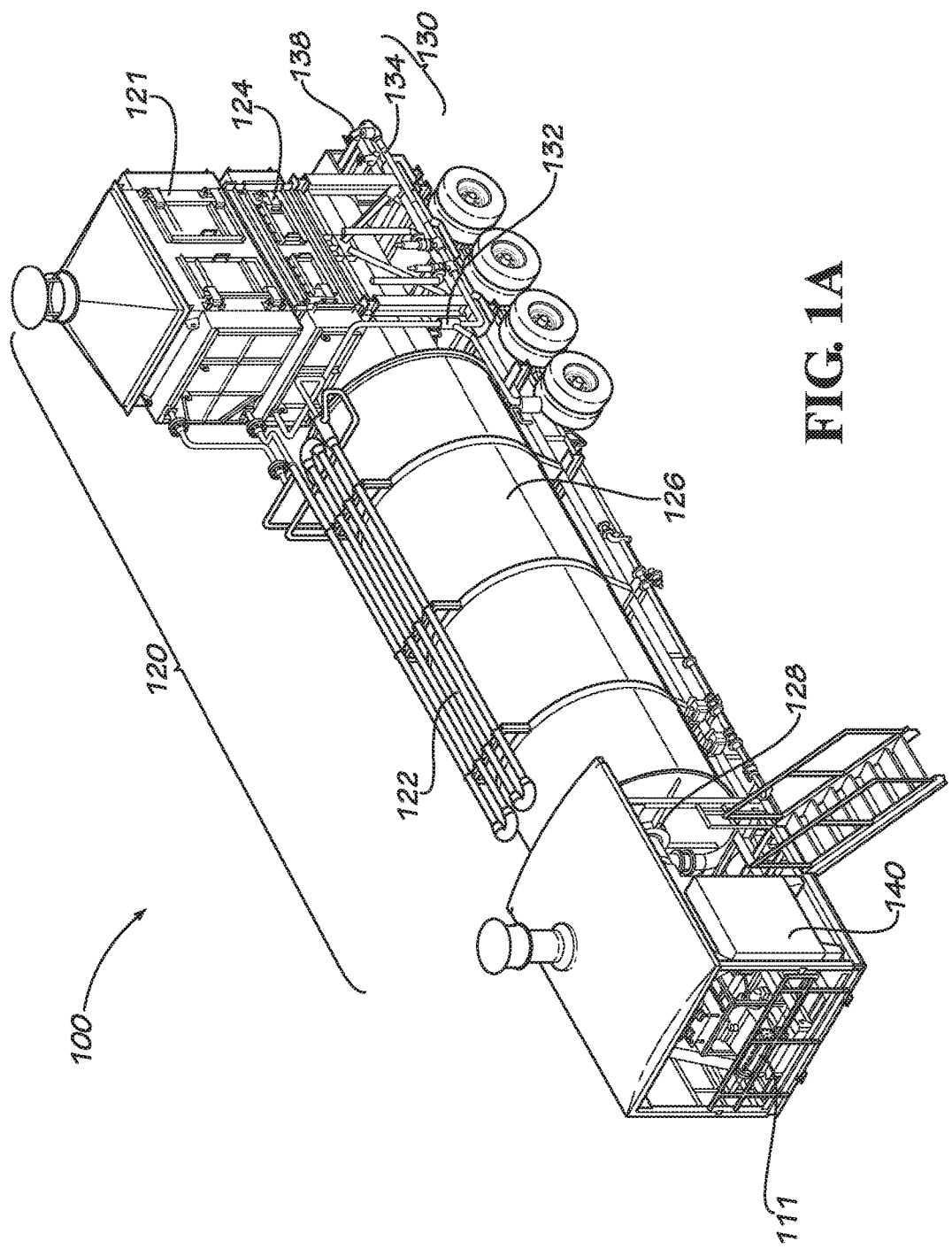

LINE DESIGNATIONS

- ---------- INSTRUMENT AIR LINES
- — — — — INSTRUMENT ELECTRICAL LEADS (W/SENSE ARROW)
- -x-x-x-x- INSTRUMENT CAPILLARY TUBING
- ———— PRIMARY PROCESS LINE
- -S-S-S-S- STEAM TRACED LINE
- -E-E-E-E- ELECTRIC TRACED LINE
- -L-L-L-L- HYDRAULIC LINE
- -O-O-O-O- SOFTWARE OR DATA LINK
- ~~~~~~~~ MECHANICAL LINK
- ∿∿∿∿∿∿ RADIATION GUIDED
- ∼∼∼∼∼∼ RADIATION UNGUIDED
  (OPTICAL RADIO, THERMAL, ETC.)

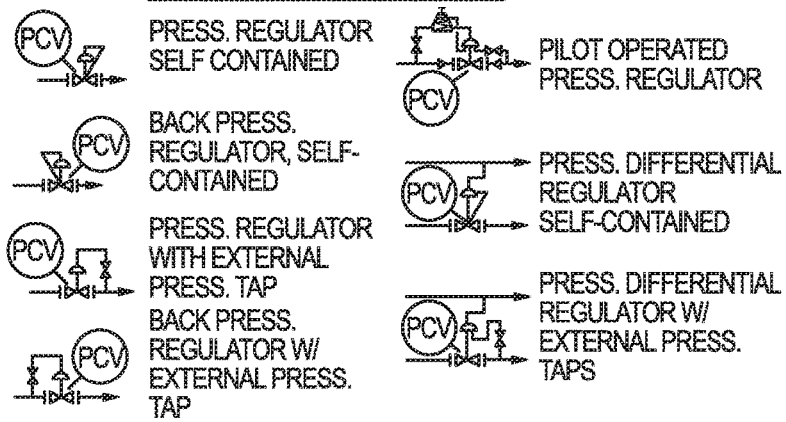

PRESSURE REGULATING VALVES

- PRESS. REGULATOR SELF CONTAINED
- PILOT OPERATED PRESS. REGULATOR
- BACK PRESS. REGULATOR, SELF-CONTAINED
- PRESS. DIFFERENTIAL REGULATOR SELF-CONTAINED
- PRESS. REGULATOR WITH EXTERNAL PRESS. TAP
- PRESS. DIFFERENTIAL REGULATOR W/ EXTERNAL PRESS. TAPS
- BACK PRESS. REGULATOR W/ EXTERNAL PRESS. TAP

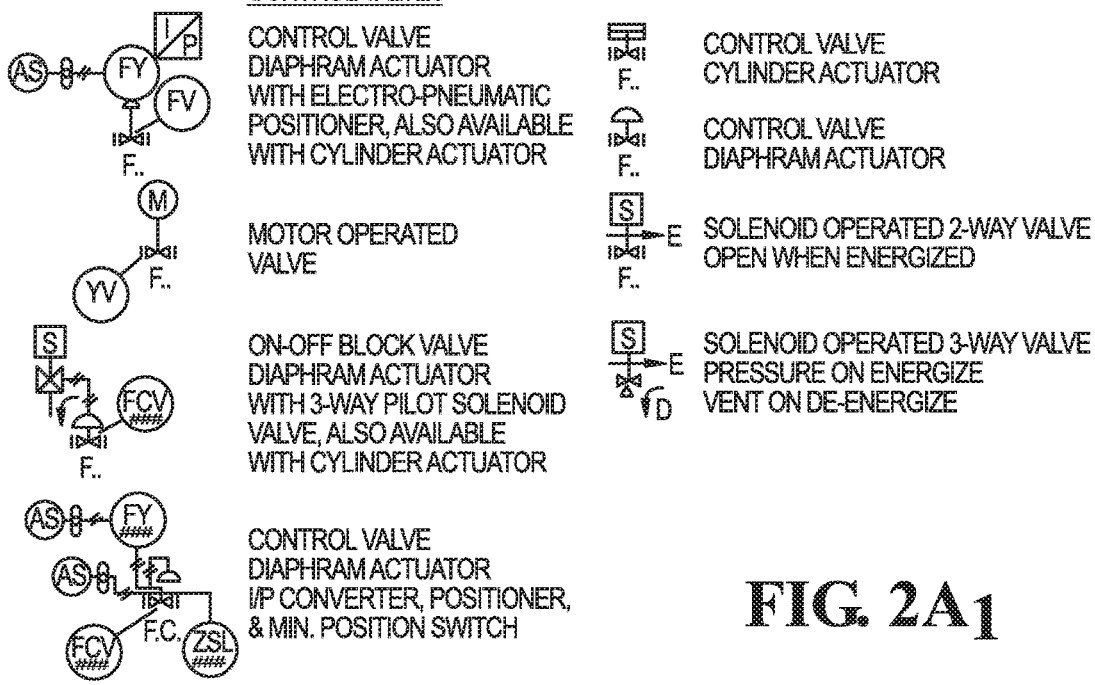

CONTROL VALVES

- CONTROL VALVE DIAPHRAM ACTUATOR WITH ELECTRO-PNEUMATIC POSITIONER, ALSO AVAILABLE WITH CYLINDER ACTUATOR
- CONTROL VALVE CYLINDER ACTUATOR
- CONTROL VALVE DIAPHRAM ACTUATOR
- MOTOR OPERATED VALVE
- SOLENOID OPERATED 2-WAY VALVE OPEN WHEN ENERGIZED
- ON-OFF BLOCK VALVE DIAPHRAM ACTUATOR WITH 3-WAY PILOT SOLENOID VALVE, ALSO AVAILABLE WITH CYLINDER ACTUATOR
- SOLENOID OPERATED 3-WAY VALVE PRESSURE ON ENERGIZE VENT ON DE-ENERGIZE
- CONTROL VALVE DIAPHRAM ACTUATOR I/P CONVERTER, POSITIONER, & MIN. POSITION SWITCH

FIG. 2A₁

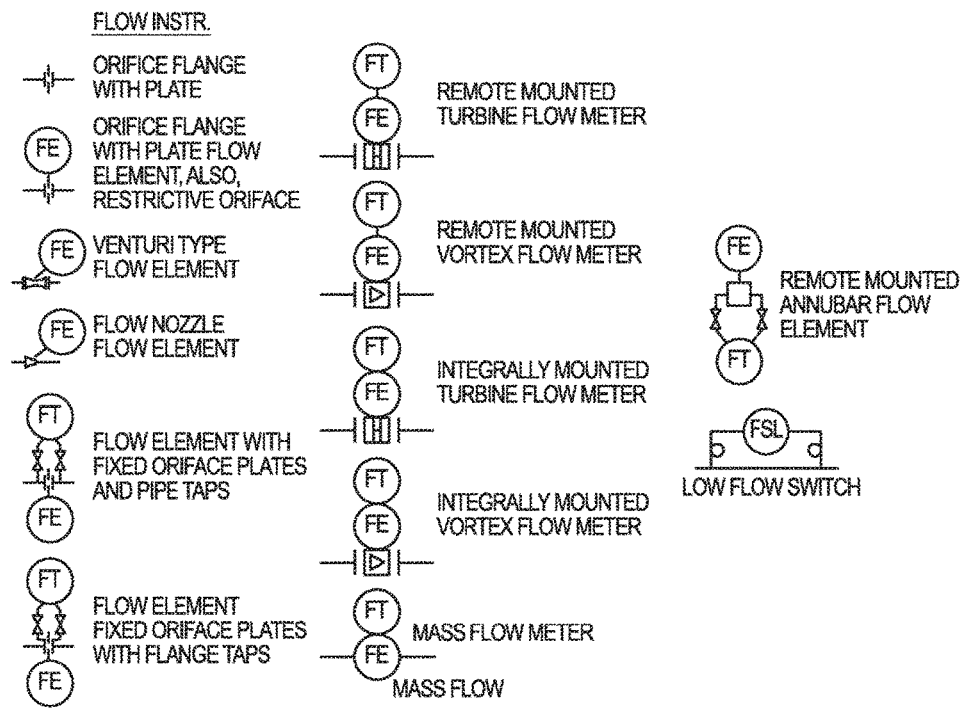
FIG. 2A$_2$

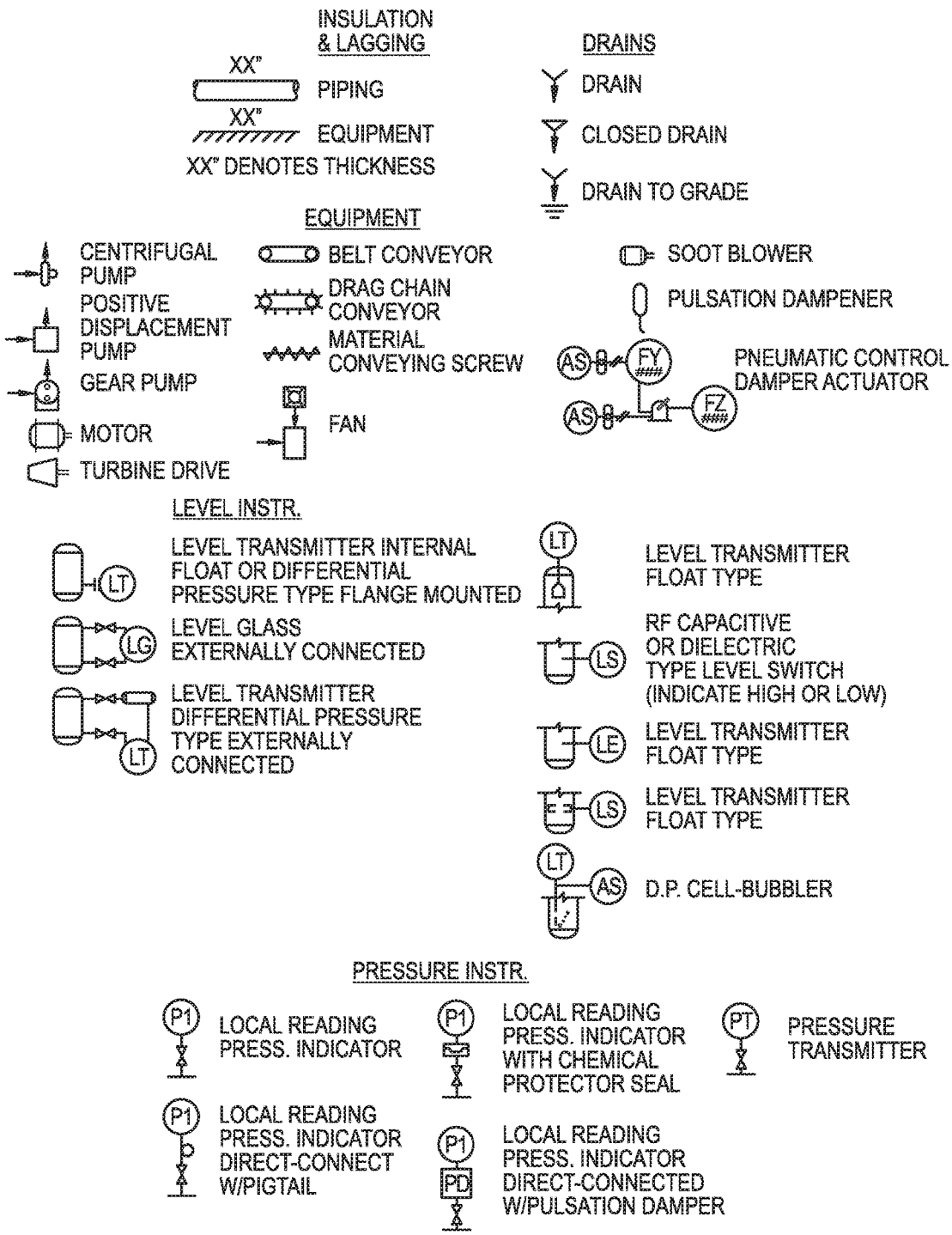
FIG. 2B₁

CONTROLS

- ○ LOCALLY MOUNTED (PROCESS CONNECTION)
- ⌀ TRANSMITTER LOCATION
- ∞ INSTRUMENT SHARING COMMON HOUSING
- ⊖ PANEL MOUNTED
- ⊖ MOUNTED BEHIND PANEL
- ▣ DISTRIBUTIVE CONTROL SYSTEM INPUT/OUTPUT (NOTE 3)
- ▦ PROGRAMMABLE LOGIC CONTROL
- ⊖ PANEL MOUNTED-AUXILLARY LOCATION
- ◯ IDENTIFICATION LETTERS SEE TABLE 1 (TYPICAL) / LOOP NUMBER (TYPICAL) (NOTE 9)
- ▱ FUNCTION BLOCK (TYPICAL) SEE TABLE 2
- ◇I UNDEFINED INTERLOCK
- ◇B BURNER INTERLOCK

TEMP INSTR.

- (T1) LOCAL READING TEMPERATURE INDICATOR
- (TT) TEMPERATURE TRANSMITTER
- (TE) RTD* TEMPERATURE ELEMENTS W/THERMOWELL *INDICATES TYPE OF ELEMENT TO BE USED

STRAINER/FILTERS

- FILTER
- CONE STRAINER
- Y-TYPE STRAINER
- FILTER / REGULATOR
- DUPLEX STRAINER

MISC. SYMBOLS

- MUFFLER OR SILENCER
- VTR VENT THRU ROOF
- VTA VENT TO ATMOSPHERE
- T STEAM TRAP (SEE PIPING DETAILS)
- HOSE CONNECTION
- CHEMICAL INJECTION QUILL
- D-? DAMPER
- STEAM HEADER CAP
- PIPE FLANGE CONNECTION
- CONDENSATE POT
- DESUPERHEATER
- KG-? KNIFE GATE
- RUPTURE DISC
- FLEX HOSE
- POSITION SWITCH-INDICATE OPEN (ZSO) OR CLOSED (ZSC) FOR SWITCHES ON VALVES
- (Q2) ANALYSIS (INDICATE MEASURED VARIABLE)
- (HS) HAND SWITCH
- (STOP/RUN) STATUS LIGHT (DEFINE IF NECESSARY FOR CLARITY)
- (AS) INSTRUMENT AIR SOURCE

FIG. 2B$_2$

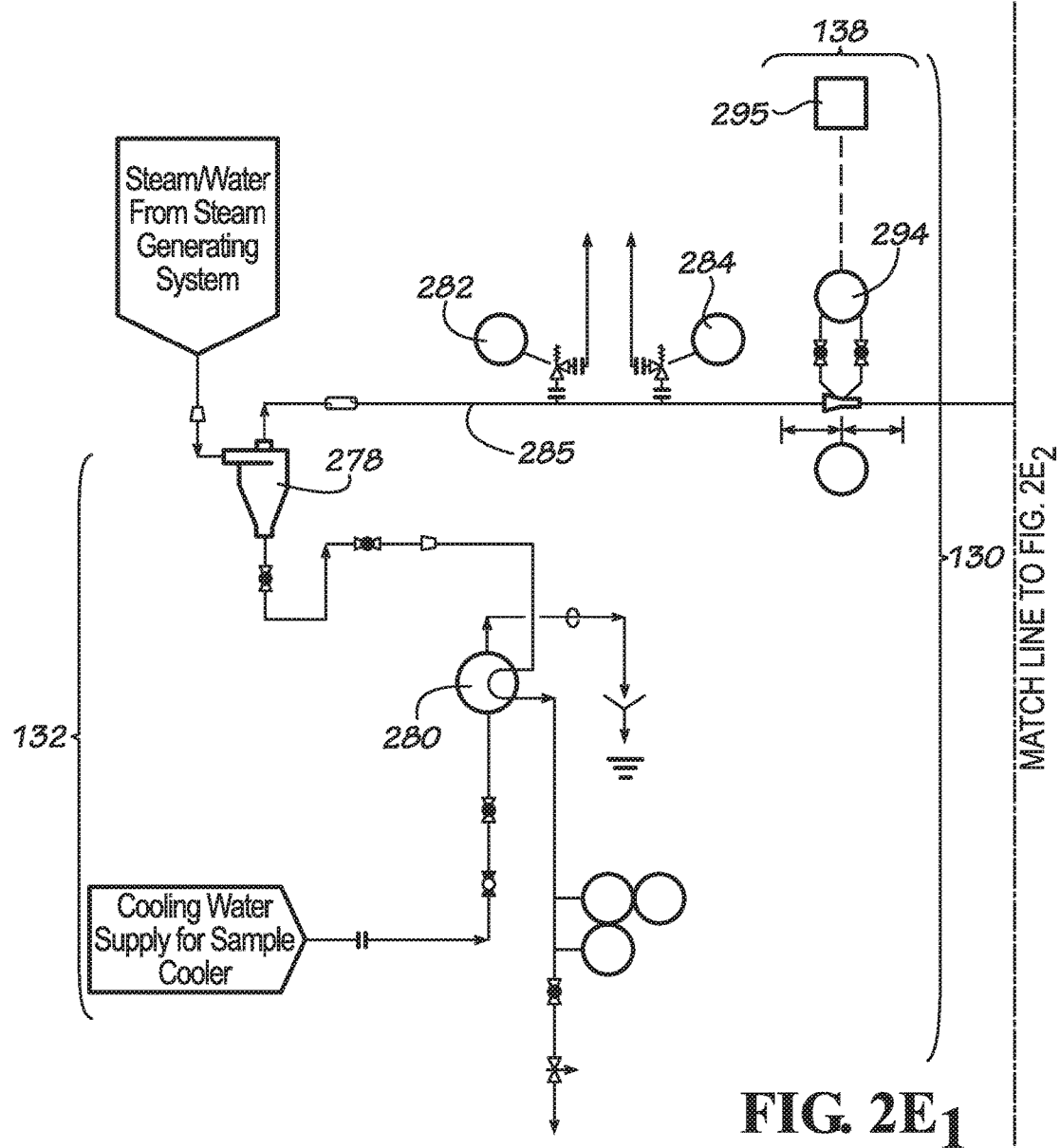
FIG. 2E₁

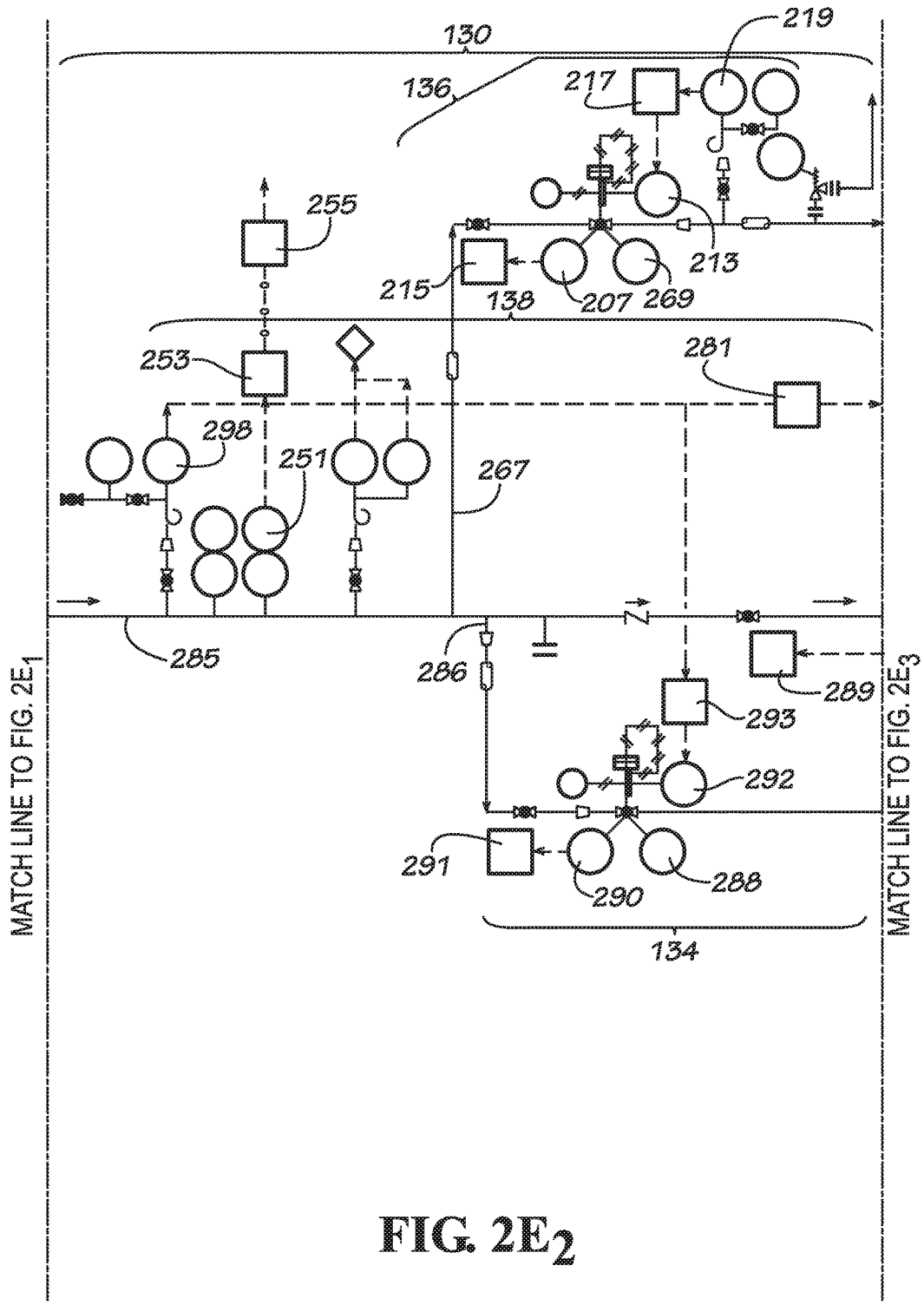
FIG. 2E$_2$

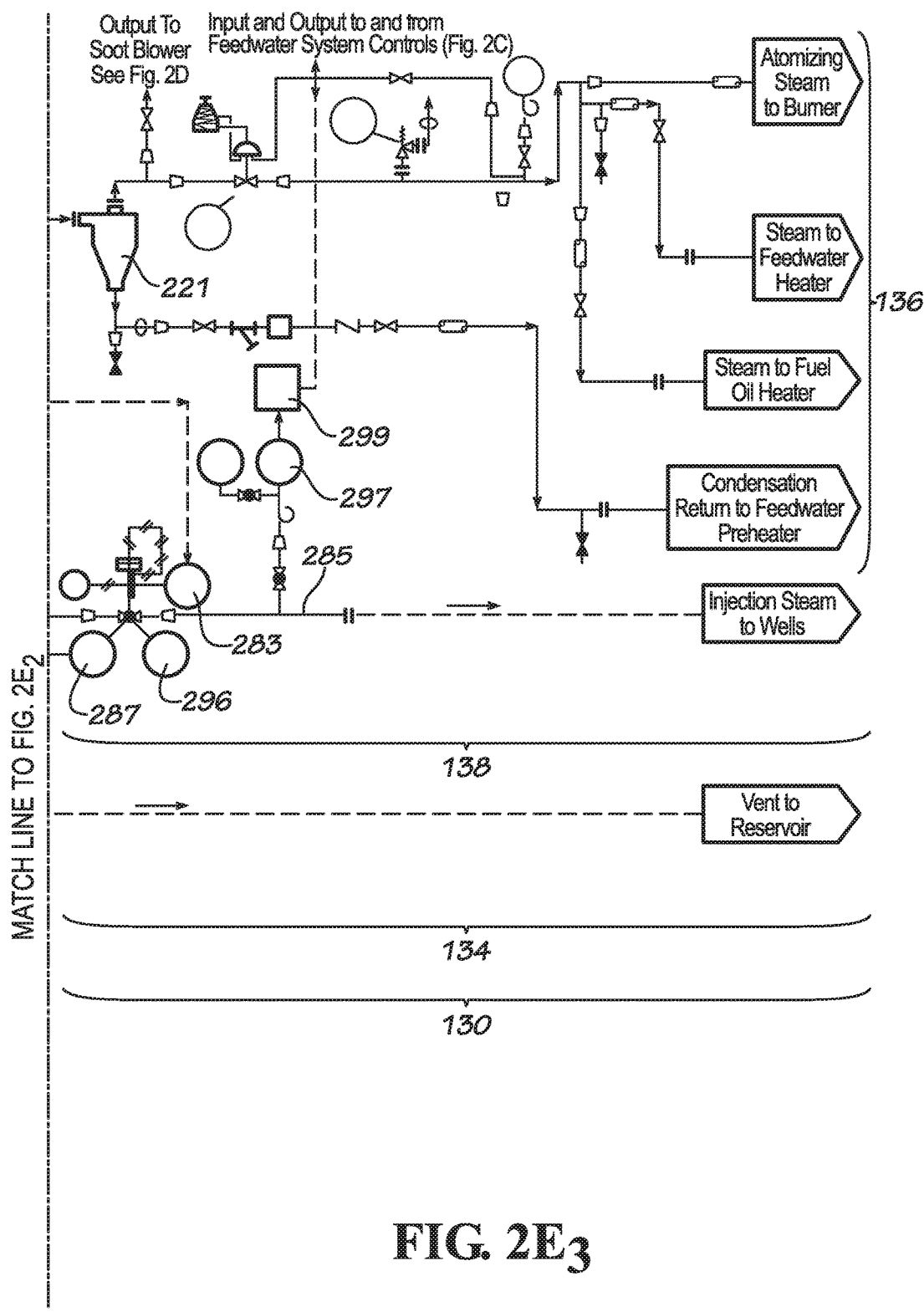
FIG. 2E₃ the art upon examination of the following detailed description and accompanying drawings. It is intended that all such systems, methods, features, and advantages be included within the present disclosure and protected by the accompanying claims.

STEAM GENERATION APPARATUS AND ASSOCIATED CONTROL SYSTEM AND METHODS FOR PROVIDING DESIRED STEAM QUALITY

REFERENCE TO RELATED APPLICATIONS

This application is a divisional of U.S. application Ser. No. 14/030,667, filed Sep. 18, 2013, which is hereby specifically incorporated by reference herein in its entirety.

TECHNICAL FIELD

The current disclosure relates to steam generation apparati and associated control systems. Particularly, the current disclosure relates to such steam generation apparati and associated control systems that are used for enhanced oil recovery.

BACKGROUND

Steam generation apparati are used in a host of industries including food preparation, cleaning, heating and power generation sectors. Another industrial sector that uses steam generation apparati includes enhanced oil recovery projects where steam is injected into the reservoir through injection wells located in rock that has fluid communication with production wells. The purpose of steam injection is to increase reservoir pressure and temperature to displace hydrocarbons toward a pumping well. This allows more oil to be recovered than was initially possible during the primary drilling and oil extraction phase of an oil well. As can be imagined, such steam generation apparati require that a number of process variables and associated equipment be controlled during startup and continuous normal operation. Accordingly, a need exists for an apparatus that manages such variables efficiently during startup and continuous normal operation.

SUMMARY

An apparatus for supplying at least one of water and steam to a desired destination at a desired steam quality comprising a feedwater system; a steam generation system; a delivery system that includes a main steam header pipe that runs from the steam generation system to the desired destination for supplying at least one of water and steam. The apparatus further comprises a plurality of instruments and devices that are in operative association with the feedwater system, steam generating system, or delivery system configured for sensing physical parameters of water or steam; and a control system having an input device, output device and memory, the control system being in operative association or communication with the instruments and devices. Said control system being configured for performing the operation of determining the enthalpy of the feedwater.

A method of predicting or attaining the desired steam quality of at least one of water and steam supplied by an apparatus capable of producing at least one of water and steam of varying quality, the apparatus including a feedwater supply system, a steam generation system and a delivery system, the method comprising the following steps: determining the feedwater enthalpy and flow rate; setting a desired value for the quality of at least one of water and steam; and estimating the enthalpy of the desired steam quality of at least one of water and steam.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIGS. 1A and 1B are different perspective views of a trailer mounted unit of an embodiment of a steam generating apparatus of this disclosure.

FIGS. $2A_1$, $2A_2$, $2B_1$ and $2B_2$ provide legends so that the other detailed schematics of embodiments of this disclosure can be more readily understood. Specifically, they convey the meaning and function of certain components represented symbolically in the schematics including valves, flow elements, flow meters, level instruments, pumps, motors, blowers, fans, turbines, dampers, pressure instruments, strainers/filters, temperature instruments, controls, and miscellaneous items.

Figure 2C:
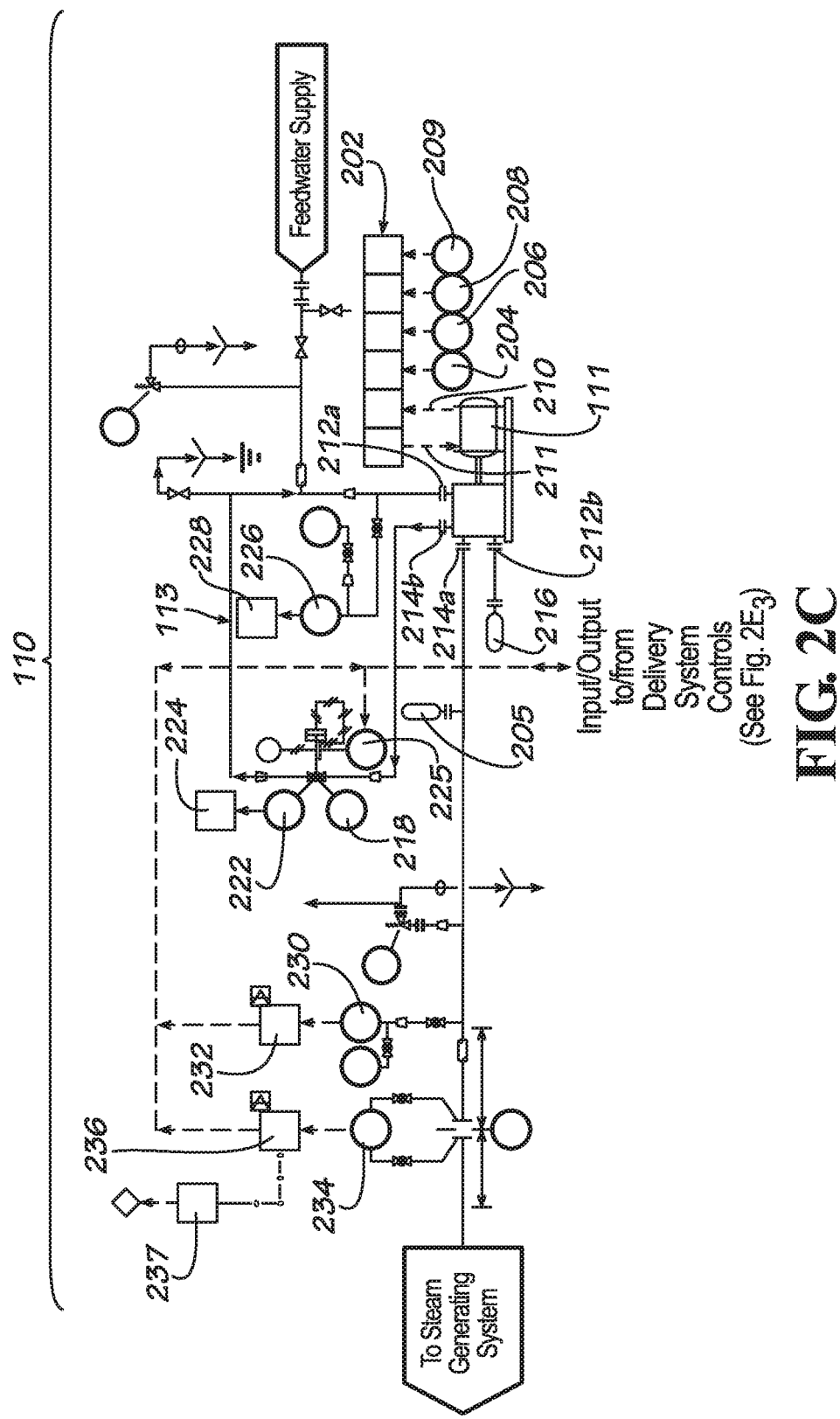

FIG. 2C is a detailed schematic of a feedwater supply system of an embodiment of a steam generating and supplying apparatus of the present disclosure.

Figure 2D:
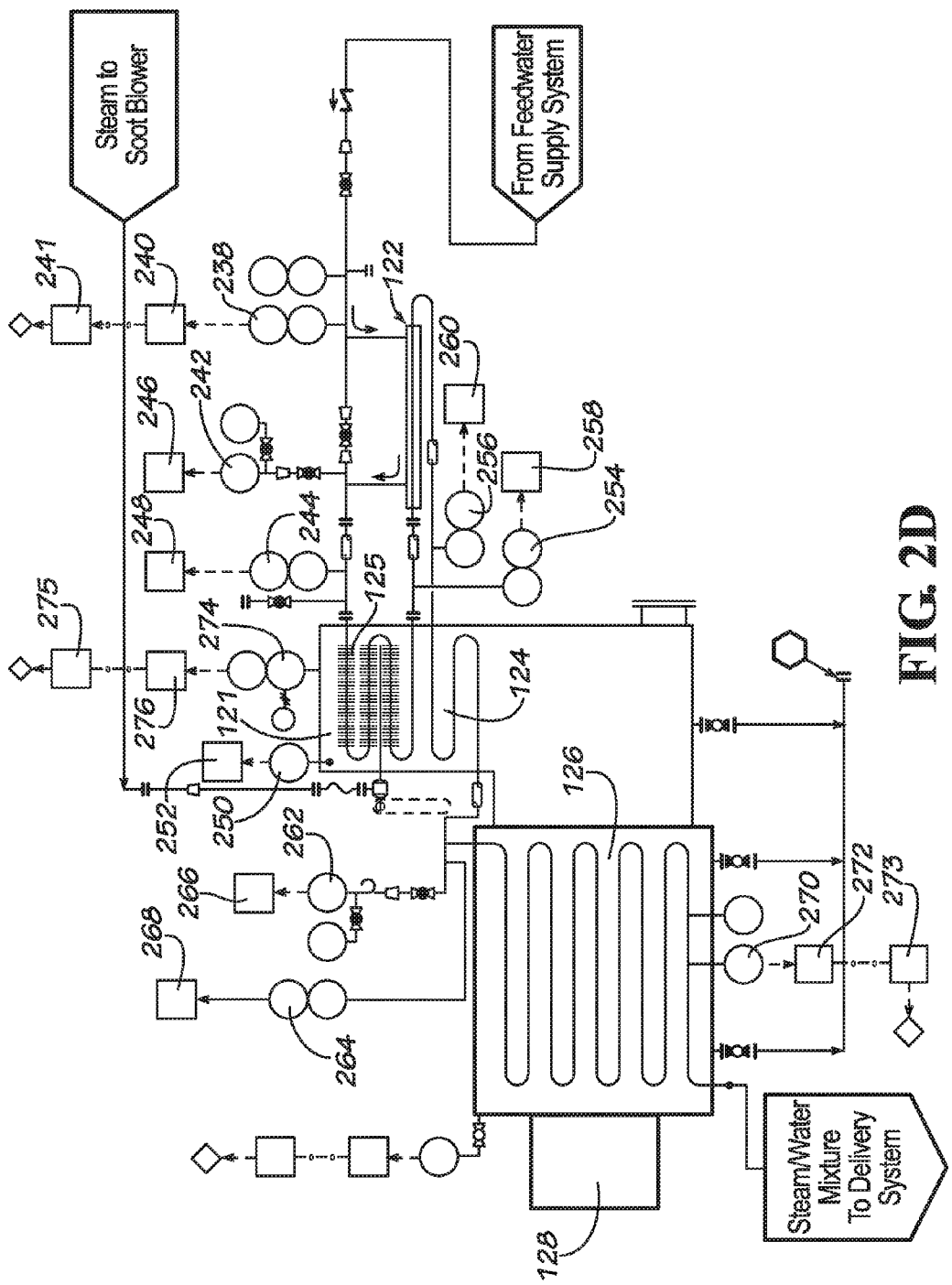

FIG. 2D is a detailed schematic of a steam generating system of an embodiment of an apparatus of the present disclosure that receives feedwater from the supply system of FIG. 2C.

FIGS. $2E_1$, $2E_2$ and $2E_3$ are segments of a detailed schematic of a steam and/or water delivery system of an embodiment of an apparatus of the present disclosure that receives steam and/or water from the steam generating system of FIG. 2D.

Figure 3A:
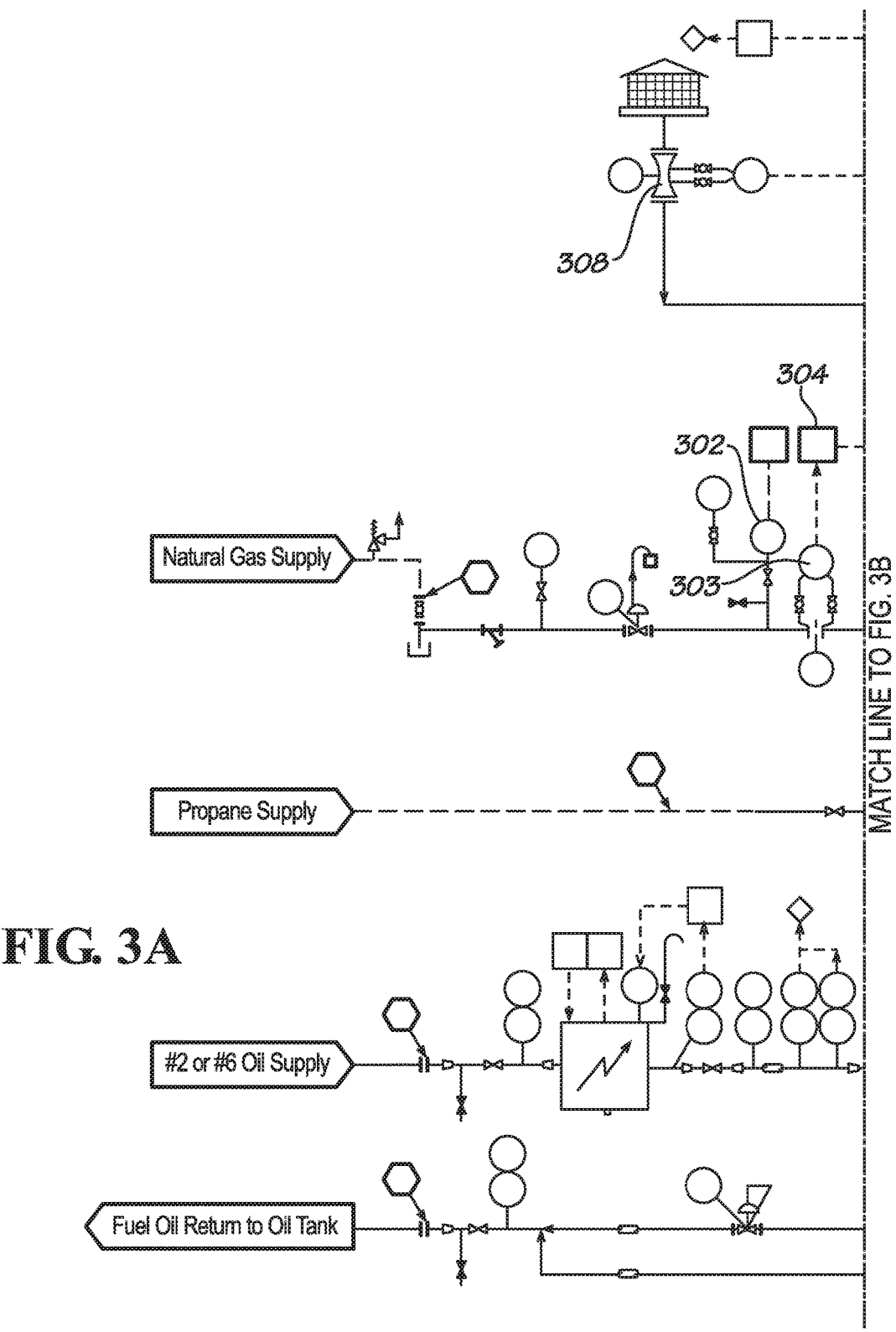
Figure 3B:
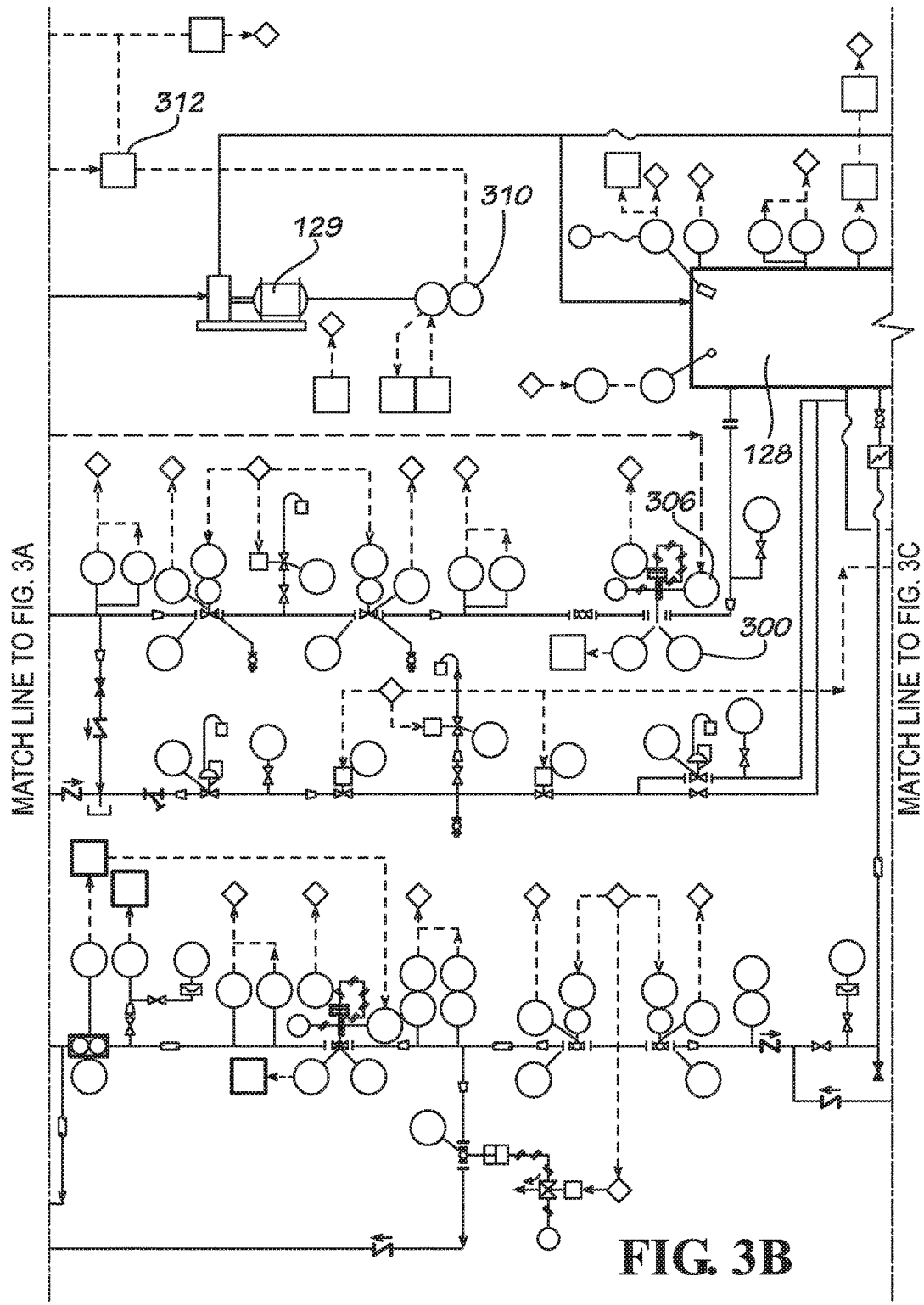
Figure 3C:
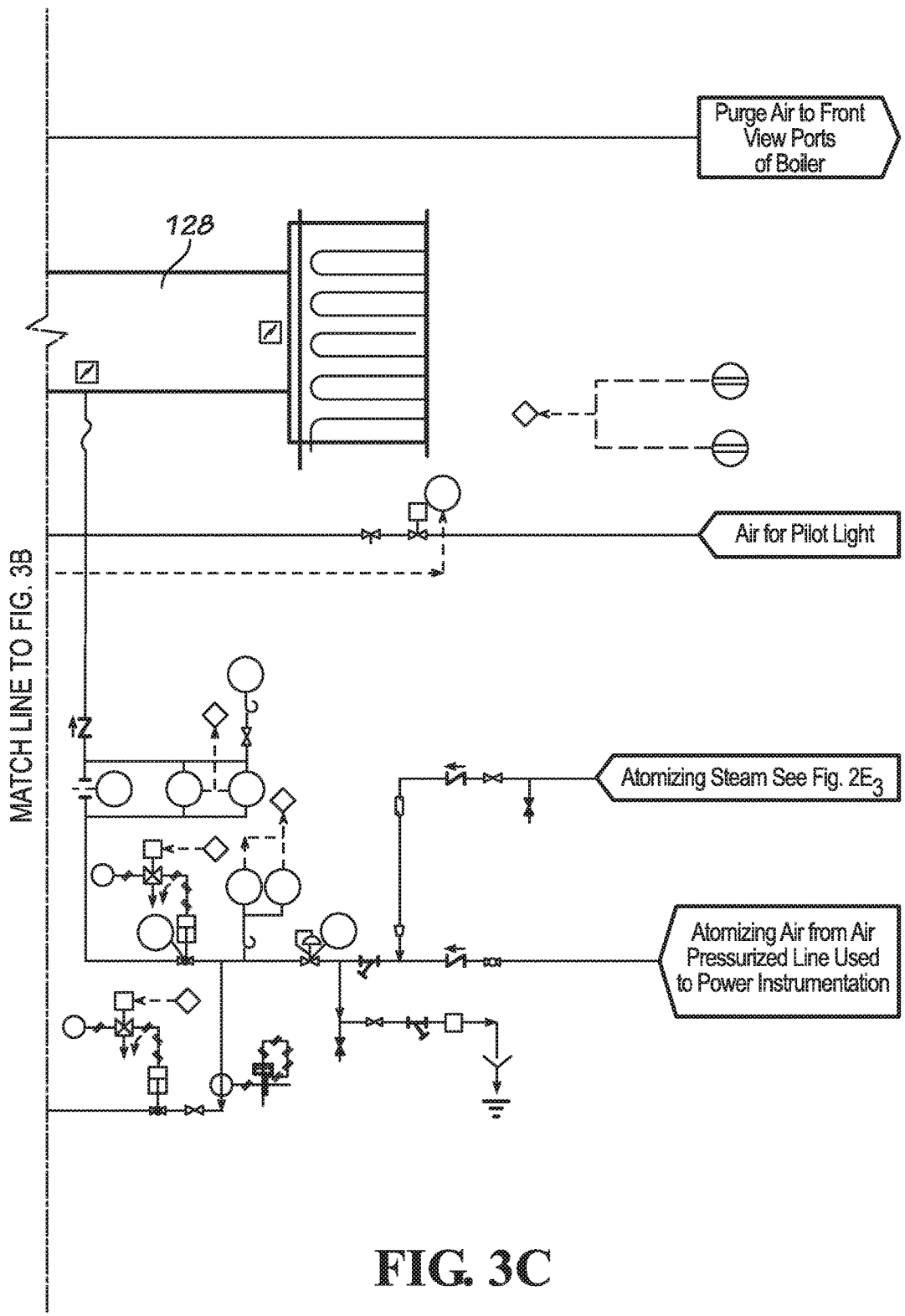

FIGS. 3A, 3B and 3C are segments of a detailed schematic of a burner of the steam generating system shown in FIG. 2D along with the associated inputs, outputs and control system.

Figure 4:
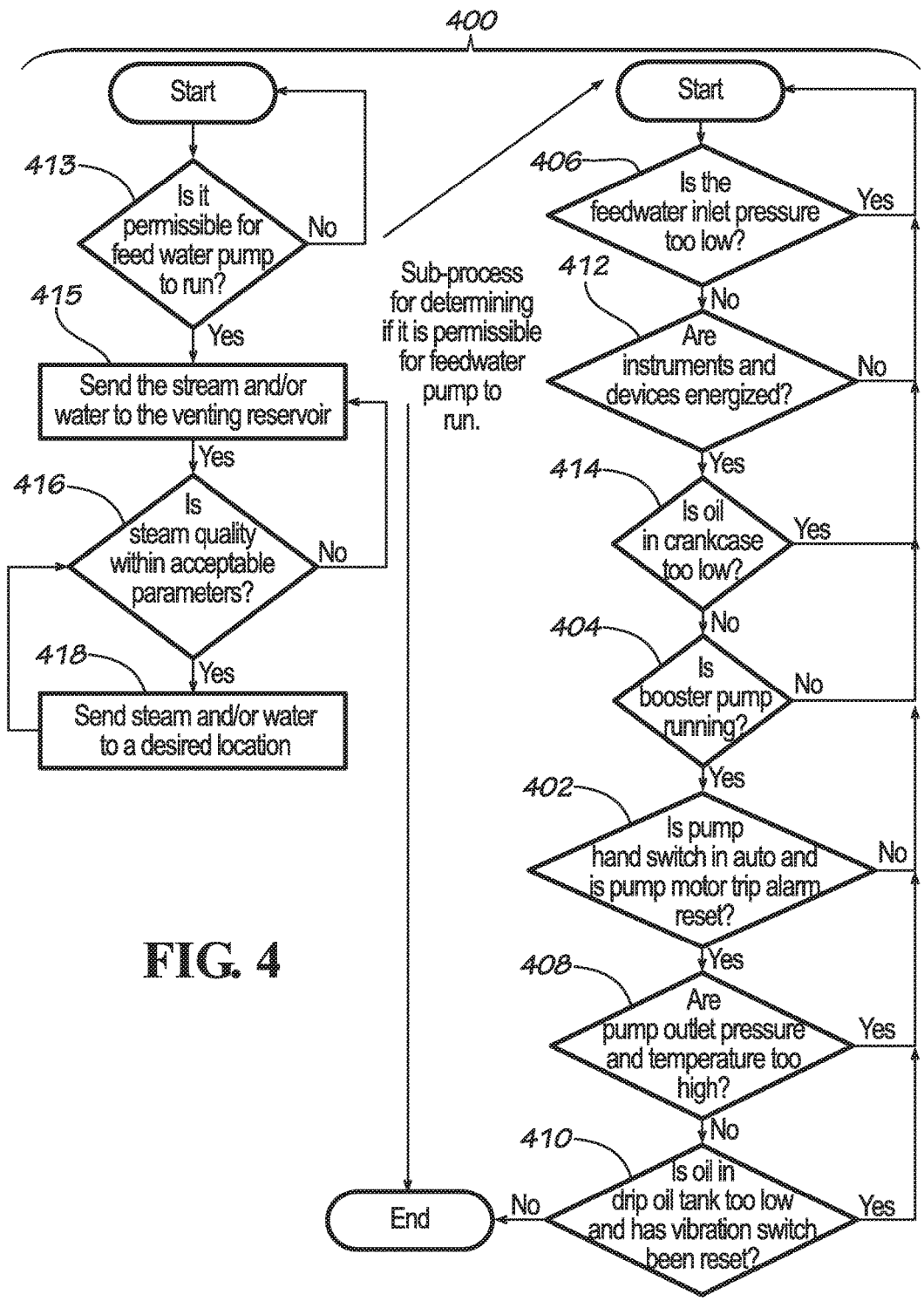

FIG. 4 is a flowchart outlining the various steps of a method for starting up a steam generating apparatus according to one embodiment of the present disclosure.

Figure 5A:
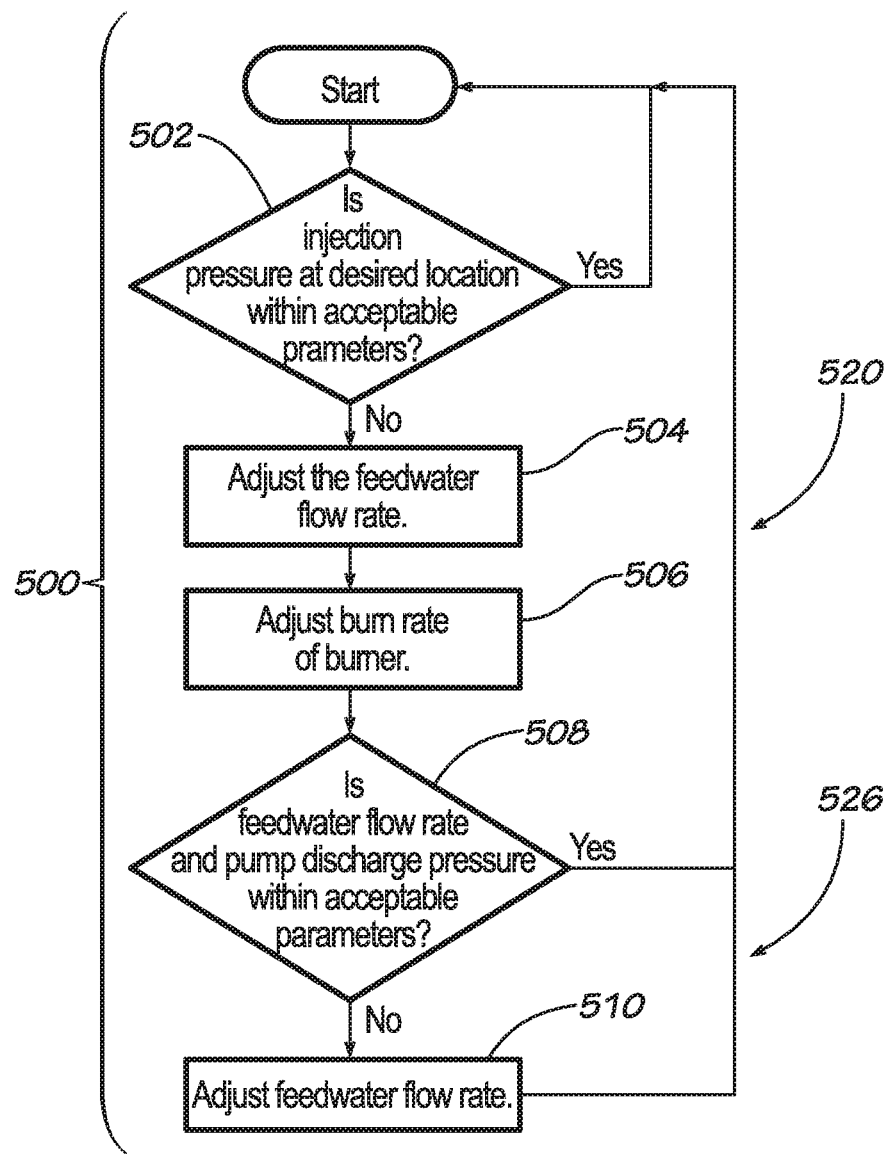

FIG. 5A is a flowchart outlining the various steps of a method or routine for attaining a desired injection pressure that is supplied by steam generating apparatus according to one embodiment of the present disclosure.

Figure 5B:
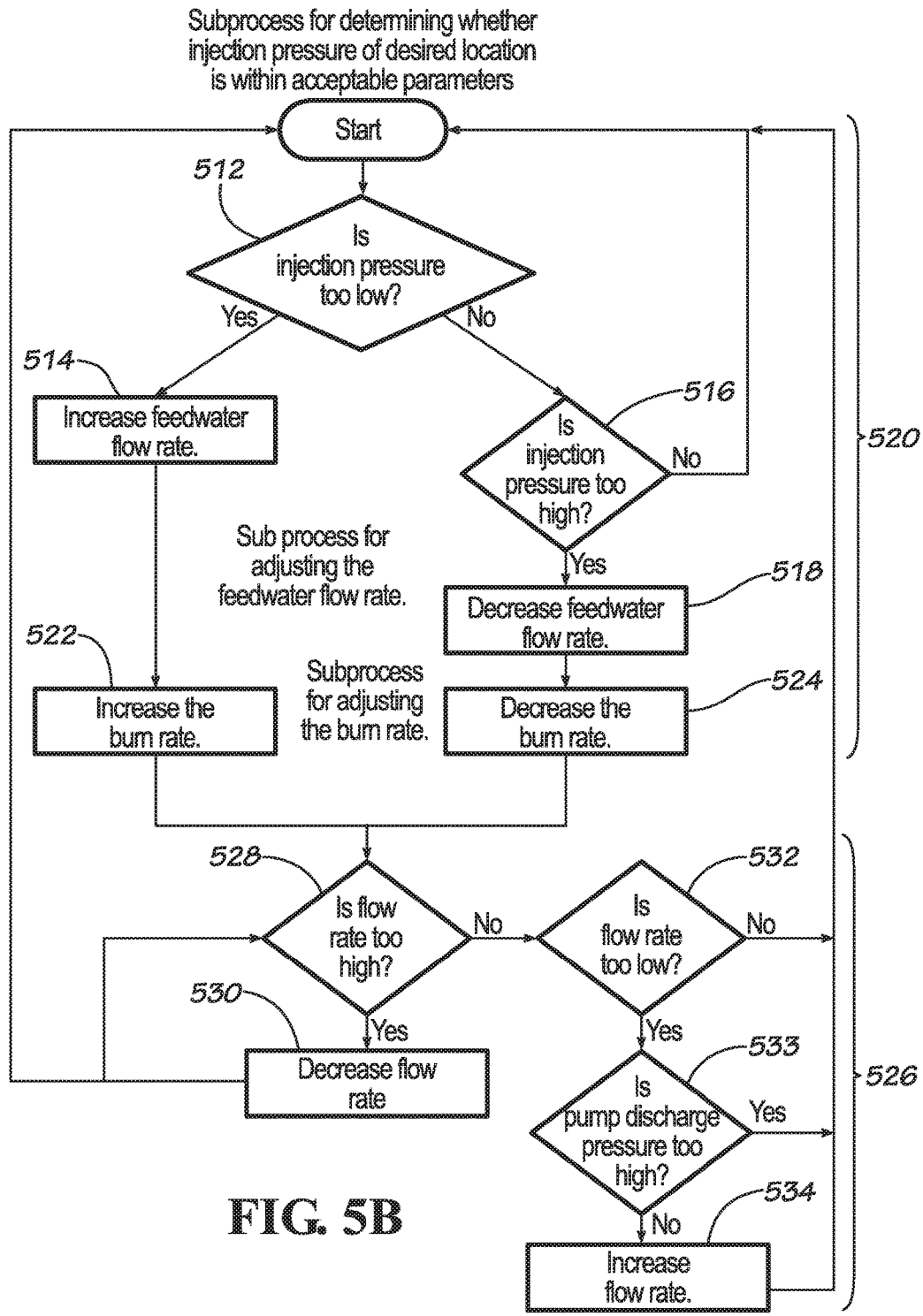

FIG. 5B is a flowchart showing the various steps of a sub-process or subroutine for the step of determining whether the injection pressure at a desired location is within acceptable parameters as shown in FIG. 5A.

Figure 5C:
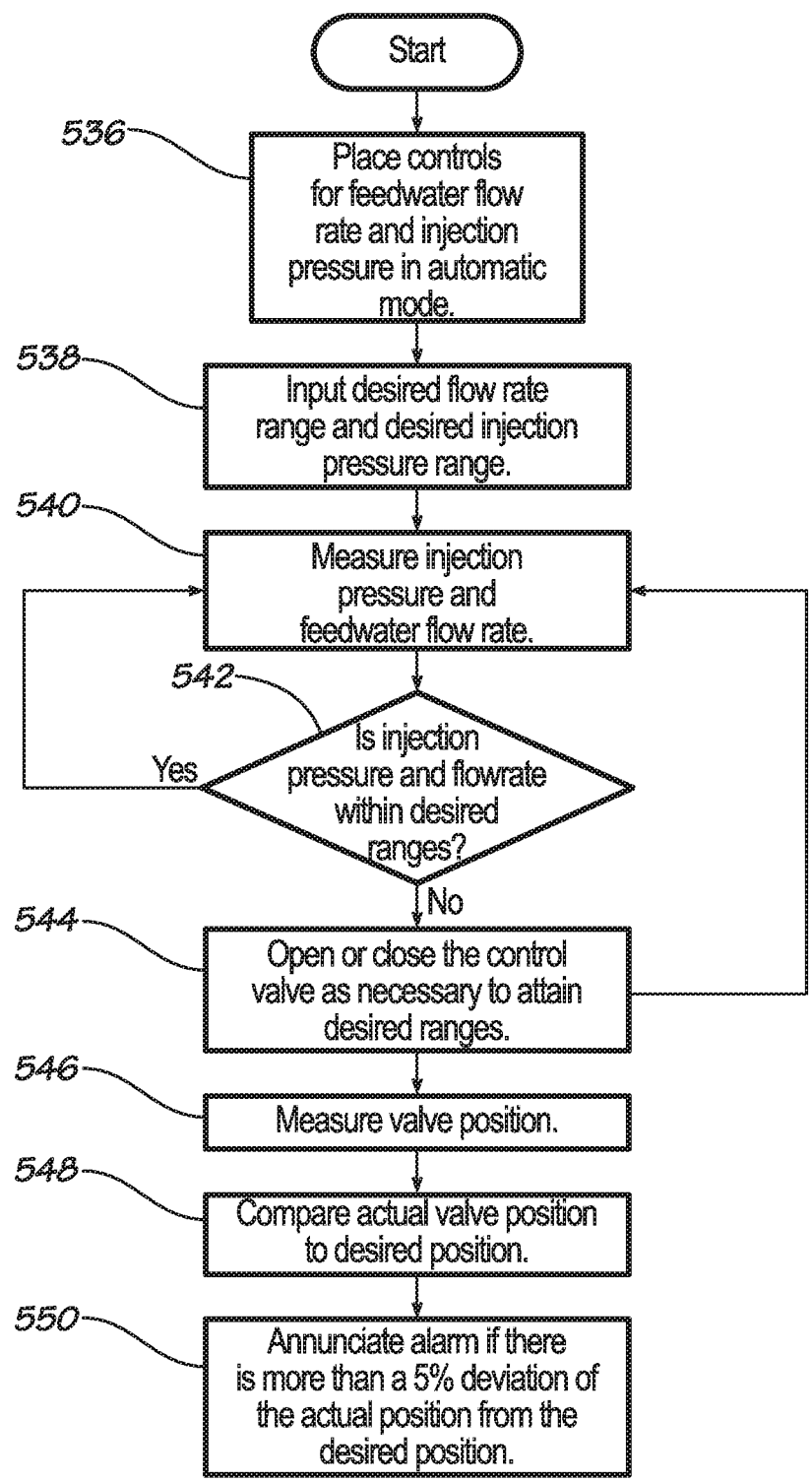

FIG. 5C is a flowchart of a method or routine similar to that disclosed in FIG. 5A wherein a control system is used and various controls for the feedwater flow rate and the injection pressure are placed into automatic mode and the desired parameters for the flow rate and the injection pressure are inputted into the control system.

Figure 6:
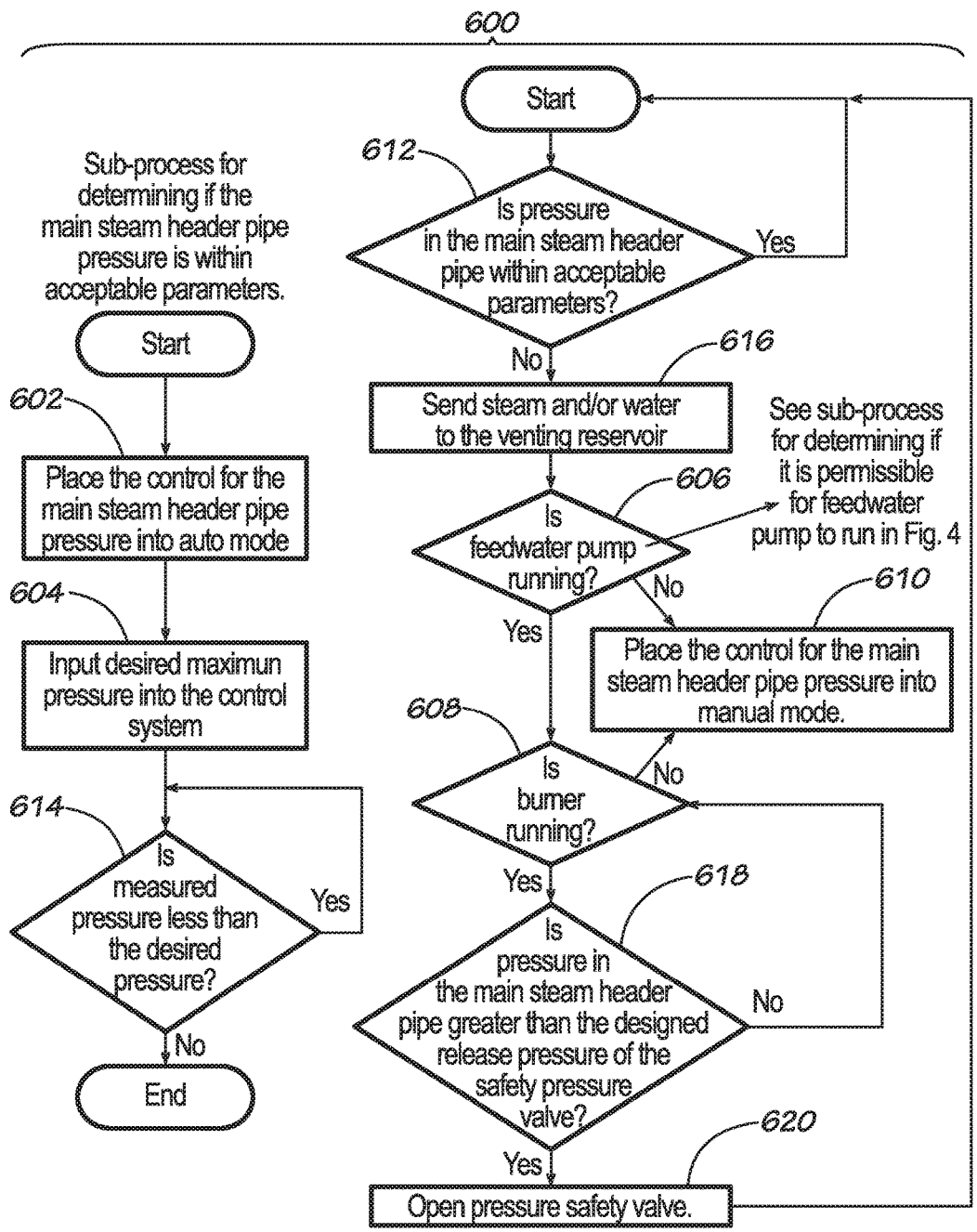

FIG. 6 contains a flowchart for maintaining the main steam header pipe pressure within acceptable parameters using a valve that is configured to send steam and/or water to a venting reservoir when needed.

Figure 7A:
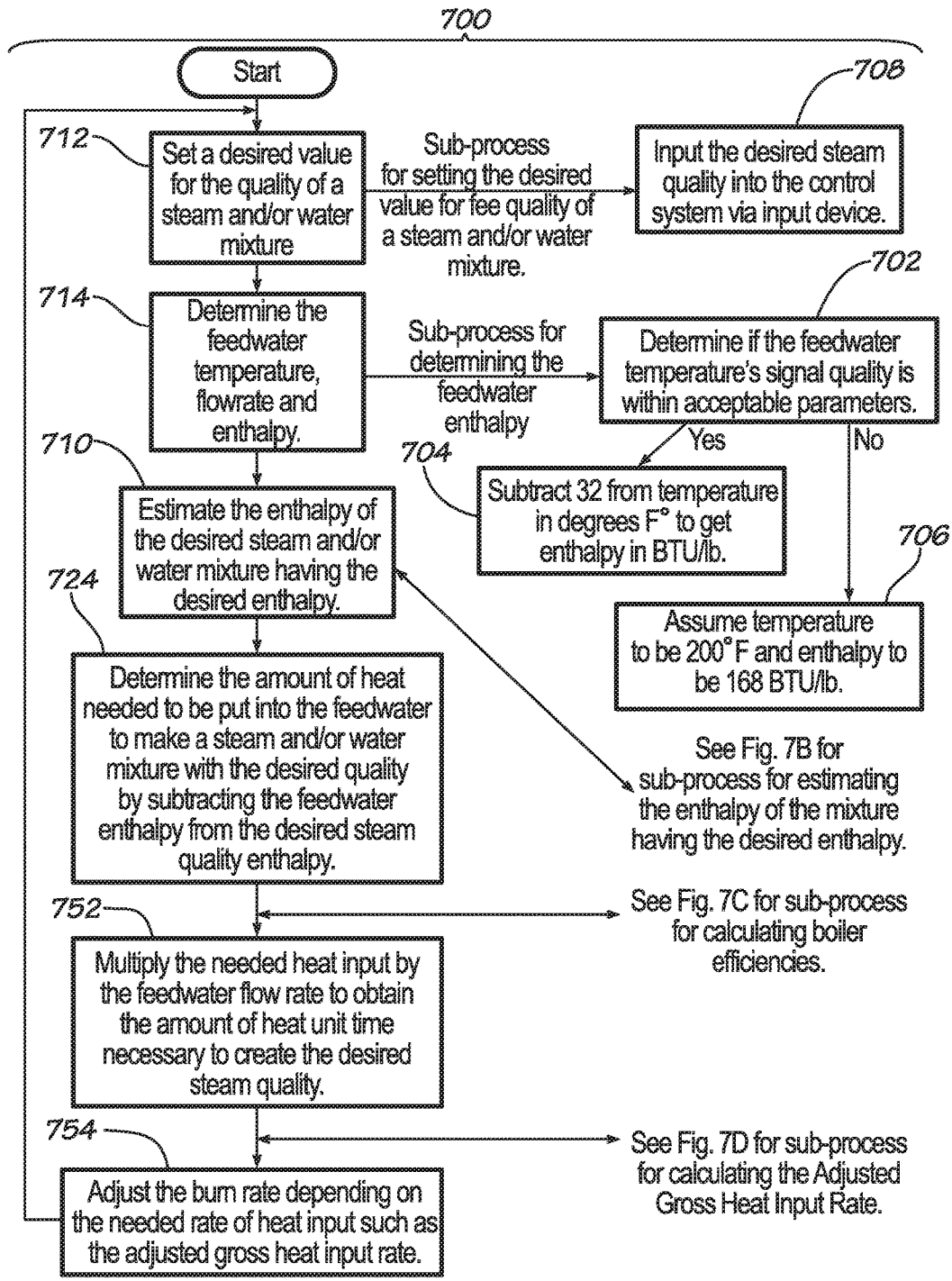

FIG. 7A shows a flowchart for a method or routine in generalized steps for predicting and attaining a desired steam quality made by a steam generating apparatus according to one embodiment of the present disclosure.

Figure 7B:
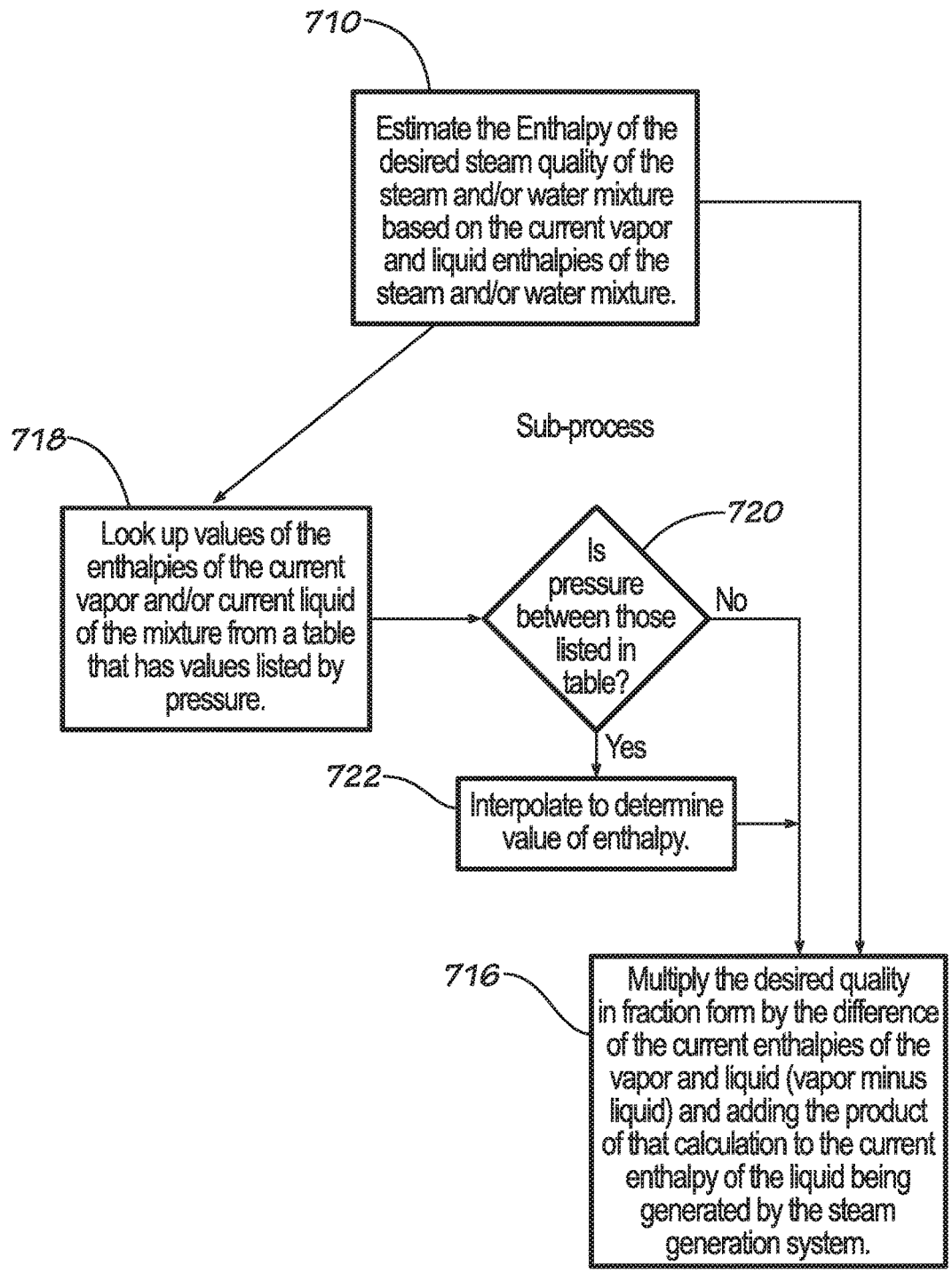

FIG. 7B shows a flowchart showing a sub-process or subroutine for the step of estimating the enthalpy of the desired steam quality of the steam and/or water mixture based on the current vapor and liquid enthalpies of the steam and/or water mixture shown in the flowchart of FIG. 7A.

Figure 7C:
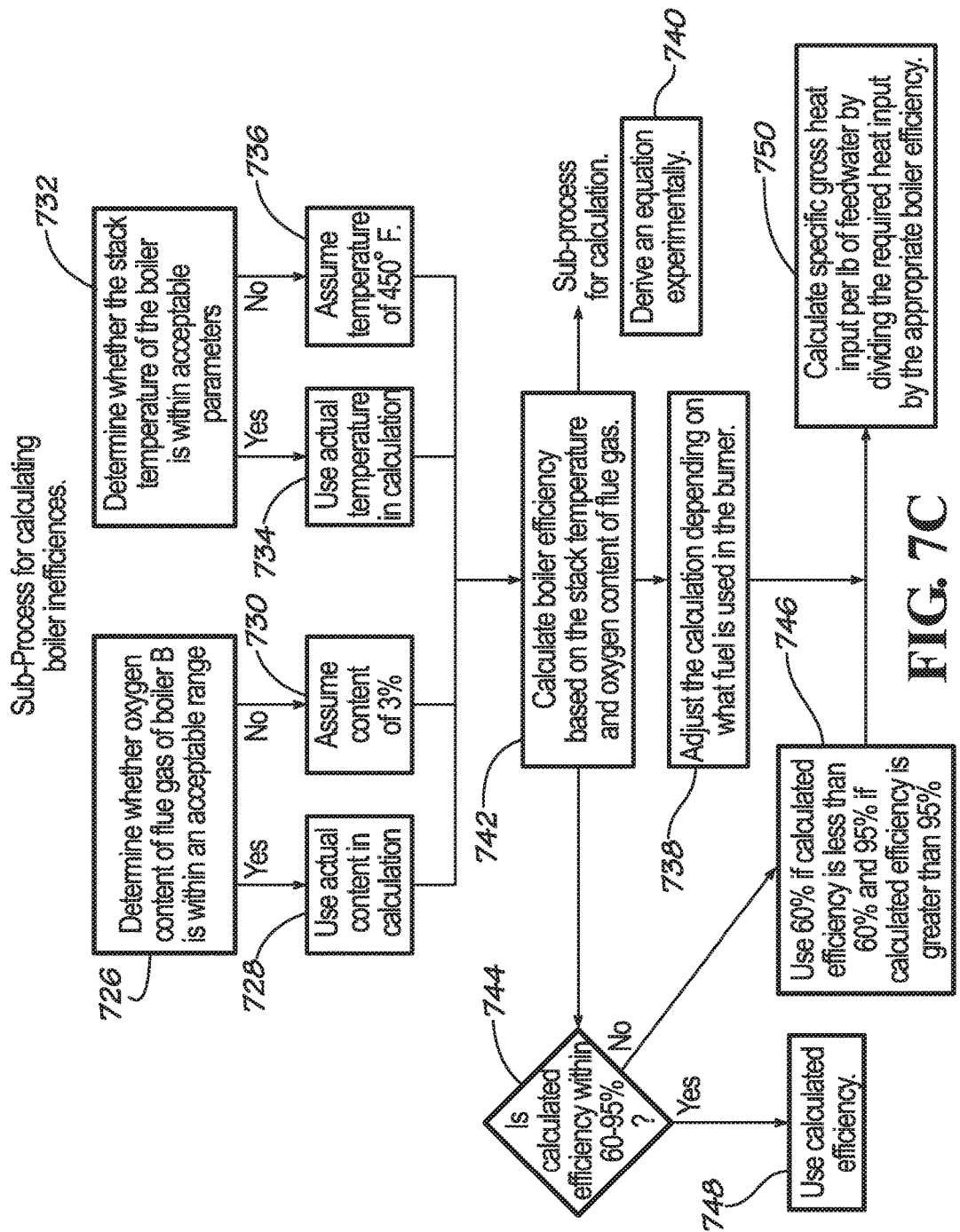

FIG. 7C depicts a flowchart showing a sub-process or subroutine for calculating boiler inefficiency that may be used to adjust the amount of heat calculated to be needed to be input to the feedwater as determined in a step of the process shown in FIG. 7A.

Figure 7D:
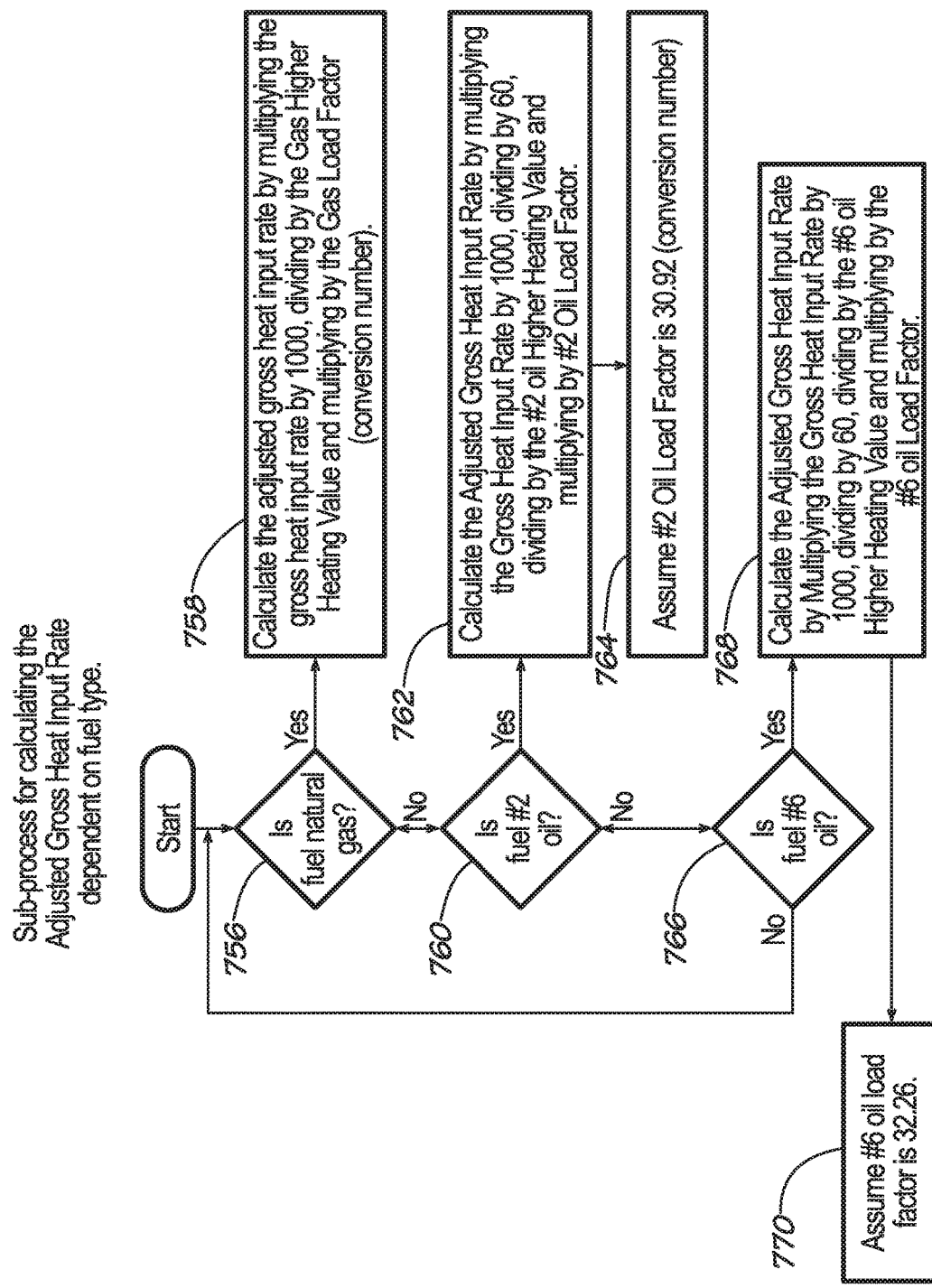

FIG. 7D shows a flowchart that illustrates the sub-process or subroutine and its associated steps for calculating the adjusted gross heat input rate depending on the type of fuel that is being used.

DETAILED DESCRIPTION

Disclosed is a steam generation apparatus, control system and associated methods, systems, devices, and various architectures. The steam generation apparatus includes a feedwater supply system, a steam generating system, a steam and water delivery system and a control system that is operatively associated and/or in communication with any or all of these systems. Also, various methods or protocols are disclosed for operating these various systems in several phases including startup and normal operation. It would be understood by one of skill in the art that the disclosed steam generation apparatus, control system and associated methods are described in but a few exemplary embodiments among many. No particular terminology or description should be considered limiting on the disclosure or the scope of any claims issuing therefrom.

Steam injection is a common method of extracting heavy oil. It is considered an enhanced oil recovery (EOR) method and is the main type of thermal stimulation of oil reservoirs. There are different forms of the technology, with the two main ones being Cyclic Steam Stimulation and Steam Flooding. Both are applied to oil reservoirs relatively shallow and that contain crude oils, which are very viscous at the temperature of the native underground formation. Steam injection is widely used in the San Joaquin Valley of California (USA), the Lake Maracaibo area of Venezuela and the oil sands of northern Alberta (Canada) to name but a few locations. Steam flood, known as a steam drive, wells are used as steam injection wells and other wells are used for oil production.

Two mechanisms are at work to improve the amount of oil recovered. The first is to heat the oil to higher temperatures and to thereby decrease its viscosity so that it more easily flows through the formation toward the producing wells. A second mechanism is the physical displacement in which oil is pushed to the production wells. While more steam is needed for this method than for the cyclic method, it is typically more effective at recovering a larger portion of the oil. Cyclic and steam flooding techniques are but a few of the methods to which the disclosed embodiments may be applied, but it is contemplated that other methods currently used in the art or that will be devised in the art could be used with the disclosed embodiments.

The intent is to reduce the viscosity of the bitumen to the point where gravity will pull it toward the producing well. Locations where such steam injection is employed vary in certain embodiments. Hence, the steam generating apparati disclosed herein may be mounted on portable platforms such as barges or truck trailers so that they can be transported to a site where oil and steam injection wells are located. In other embodiments, the steam generating apparatus is located permanently at the site. Of course, the embodiments disclosed herein are not limited merely to oil recovery applications, which include both the Steam Flooding and Cyclic techniques as well as others, but it is contemplated that the embodiments discussed herein may be applied to other industrial sectors as well. Also, the quality of the steam, which is the mass fraction in a saturated mixture that is vapor, produced by the embodiments disclosed herein may be varied from 0 to 100 percent. In many applications, the desired steam quality ranges from 50 to 100 percent and may be as high as 80 to 90 percent.

Figure 1B:
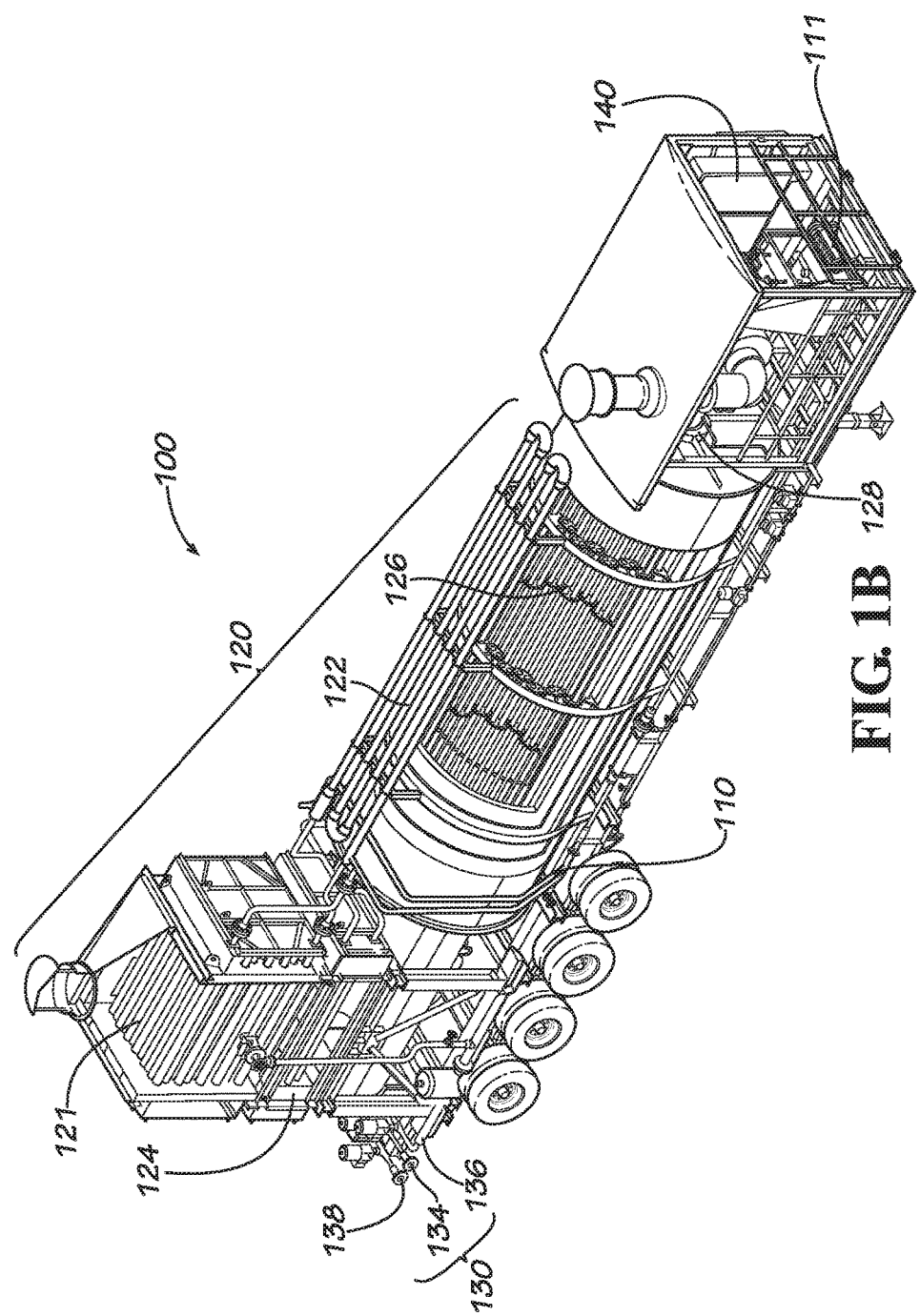

One embodiment of a steam generation and supply apparatus 100, which is at least partially portably mounted on a trailer platform, is disclosed and described in FIGS. 1A and 1B. The steam generation and supply apparatus 100 includes three major systems including the feedwater supply system 110, the steam generating system 120, and the steam and water delivery system 130.

The feedwater supply system 110 includes a water tank (not shown), a filtration device (not shown), a preheater (not shown), a booster pump 118 (shown in FIG. 1C) and a main feedwater pump 111. In general terms, water is supplied on site from a fresh water source such as a lake or municipal water system where it is stored in a water tank and then drawn out or pumped out by the booster pump 118 before being filtered for the removal of sediment and other impurities via the filtration device that could adversely affect the equipment of the apparatus. It is preferable if the water is free from impurities, that is to say, is on the level of water filtered by a reverse osmosis device and softened. The water is then heated slightly by the preheater and the flow rate and pressure of the feedwater is then increased by the main feedwater pump 111 so that it can properly supply the steam generating system 120. In certain embodiments, the feedwater pump is a positive displacement multi-plunger style of pump.

The steam generating system 120 includes a pipe in pipe (PIP) heat exchanger 122, a convection section that comprises an extended surface economizer type heat exchanger 121 and a bare tube type heat exchanger section 124, a radiant heat exchanger section 126 and a burner 128. Again, in general terms, the feedwater enters the PIP heat exchanger 122 where its temperature is increased by water already heated as their separate flow paths pass each other in a counter-flow arrangement, which is advantageous, as it is an efficient way to heat the incoming feedwater as well as help prevent combustion gases from condensing on the cold tubes found in the extended surface economizer section, which could create acid in the boiler that could damage the equipment. The water then enters the extended surface economizer 121 which includes fins or other types of extended surfaces for improving heat transfer that help to increase the water temperature further by supplying more surface area to facilitate heat transfer to the water. The water then exits out of the extended surface economizer 121 back into PIP exchanger 122 past the incoming water in a manner already described, which cools the water back down again a slight amount which is advantageous as it is not desirable to overheat the water and have 100% steam quality in the boiler. The water then enters the bare tube section 124 and then the radiant section 126 of the steam generator whose heat is created by the burning of fuel provided by the burner 128. The bare tube section lacks fins as the combustion gases in the boiler unit in this area would be too high and would melt the fins. At this point, the majority of the water has been converted to steam. As will be discussed in more detail later herein, the fuel rate supplied to the burner is monitored and controlled to adjust the amount of heat generated.

However, it is contemplated that other methods or devices known in the art or that will be devised in the art could be used to heat the water to steam including electric heating, solar heating, etc. Accordingly, the phrase "steam generation system" or apparatus should be construed broadly herein to include any method or device that is used to heat water.

Figure 1C:
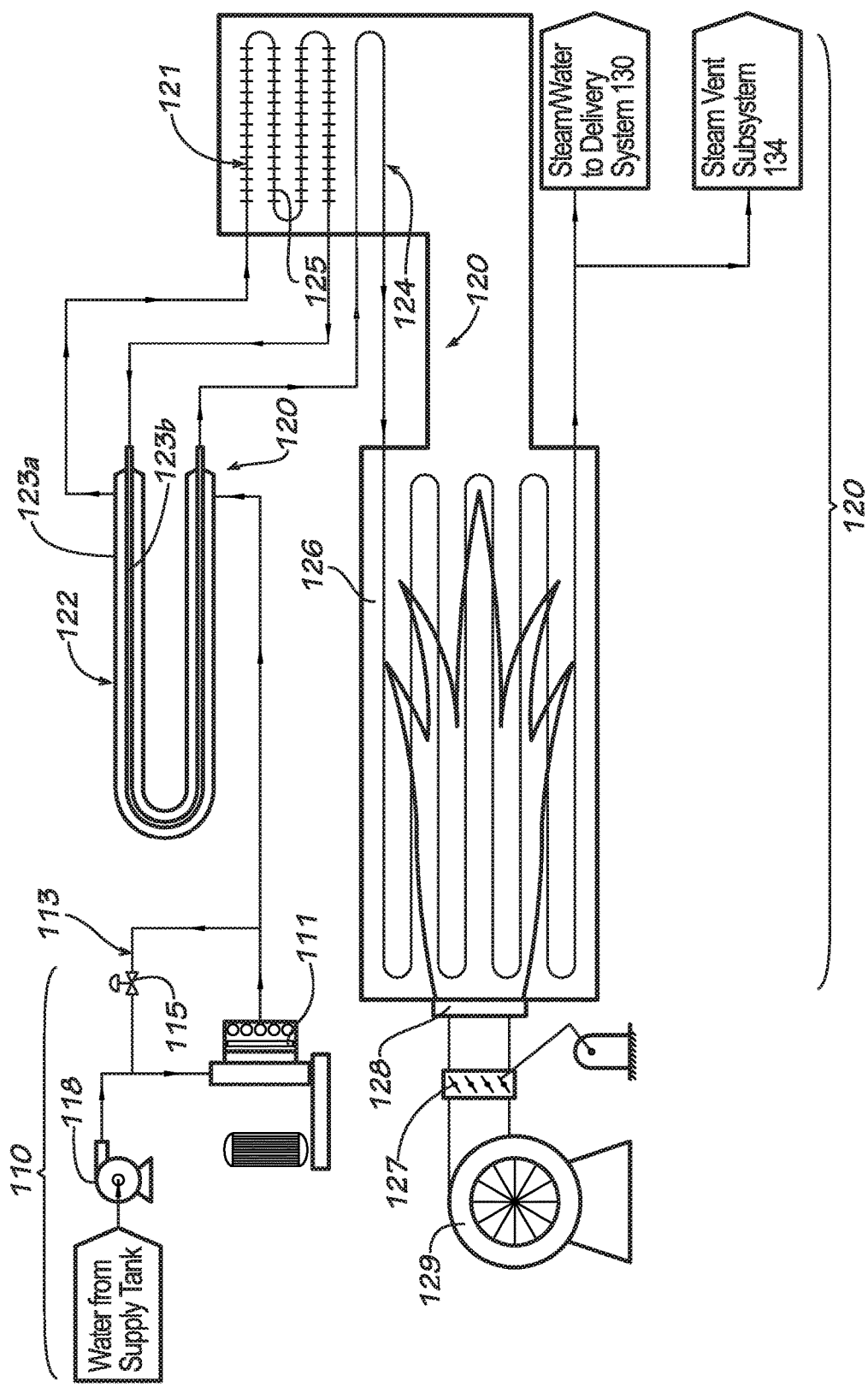
FIG. 1C is a simplified schematic of a feedwater supply system and a steam generation system of an embodiment of a steam generating and supplying apparatus of this disclosure.

Turning now to FIG. 1C, the components of the feedwater supply system 110 and the steam generating system 120 and the manner in which they work together is shown in a simplified schematic format. Water is drawn by the booster pump 118 from a preheated water supply (not shown) to the feedwater pump 111. The feedwater pump 111 then raises the pressure and flow rate of the water before it reaches the steam generating system. A feedwater flow rate control loop 113 is provided with a valve 115 so that the pressure and flow rate of the feedwater can be controlled by opening or closing the valve 115 which effectively changes the amount of water sent toward the steam generating system 120. The functioning of this control loop will be discussed in more detail later.

The feedwater then enters the PIP heat exchanger 122 into an outer pipe 123a that surrounds an inner pipe 123b, allowing the colder water that is entering the PIP heat exchanger 122 to run past warmer water found in the inner pipe 123b in an opposite direction. As previously described, this inner water has already been heated to a higher temperature by the extended surface economizer 121 of the steam generating system 120. Leaving the outer pipe, the water then enters the extended surface economizer 121 that includes a region having fins 125 and returns to the PIP heat exchanger 122 through the inner pipe 123b. The water then passes through the bare tube section 124. The water then exits the bare tube section and passes back through the PIP heat exchanger 122 and then enters the pipe found in the radiant section 126, where the water is heated through radiation by a flame created by the burner 128 that has fuel supplied to it as well as air via the combustion air damper 127 and supply fan 129. The damper actuator controls the position of the air damper 127 which comprises a series of louvers that move to an open position. This in turn, regulates the amount of air entering the burner 128. Alternatively, the air flow is regulated by controlling the speed of the supply fan with a variable frequency drive that is run by the control system.

Focusing back now on FIGS. 1A and 1B, the water and steam delivery system 130 includes a steam quality measuring subsystem 132, a venting subsystem 134, a bleed-off or diverter subsystem 136, and a steam injection subsystem 138. In overview, the steam quality measuring system 132 allows for a sample of the steam and water mixture that exits the steam generating system 120 to be cooled down and analyzed by methods or devices commonly known in the art to see what portion of the mixture is in fact steam. The venting subsystem 134 provides an avenue for venting steam and/or water to atmosphere and/or a reservoir when certain parameters are not within acceptable limits both during startup and during normal operation. The bleed-off system 136 allows a portion of the steam and water mixture to be separated from the mainline of the delivery system so that it can be fed to auxiliary equipment and/or recirculated to the feedwater preheater. Finally, the steam injection subsystem 138 provides the steam/water mixture to an injection well at a desired pressure and quality. More details of how the delivery system 130 works will be given later.

Furthermore, a control system 140 is provided that can help ensure that the quality of the steam/water mixture as well as its temperature and pressure is within desired parameters as it is injected into an injection well. In particular, the control system helps execute several algorithms or implements various routines, processes, and methods described herein that control operation of the apparatus 100 and that improve the efficiency as well as the safety and durability of the apparatus 100. For this embodiment, the control system includes a series of control units that are in communication with each other through the programmable logic controller (PLC) and certain components of the apparatus. The PLC (Allen Bradley Series No. L1756) is programmed as desired. However, it is contemplated that the control system could be provided by any other devices or methods known in the art or that will be devised in the art as is elaborated upon later herein. In other embodiments, the control system may include a series of control units, instruments, control devices and other components that are communicatively connected to a programmable logic controller (PLC). the PLC may represent any PLC known in the art, a general-purpose processor with a firmware or other memory containing processing logic, a field-programmable gate array ("FPGA"), a distributed control system ("DCS"), or the like.

The control system may further implement input devices, such as a touchscreens, keyboards, trackballs, mice, switches, knobs, and the like, and output devices, such as displays, dials, gauges, audible and visible alarm annunciators, and the like, that are in communication with the PLC. As described herein, a "memory" includes any non-transitory computer-readable medium accessible to the PLC or other processor of the control system and used to store data structures, program modules, and other processor-executable code or logic, and does not include transitory signals. As such, memory may include, but is not limited to, RAM, ROM, EPROM, EEPROM, flash memory or other solid-state memory technology, optical disk storage technology, hard disk devices ("HDD") or other magnetic disk storage, other magnetic storage devices, and the like. In further embodiments, the control system could be provided by any other devices or methods known in the art or that will be devised in the art that may implement the routines, processes and methods described herein for controlling the operation of the apparatus 100 as well as improving the efficiency, safety, and durability of the apparatus, including a general purpose computer communicatively coupled to the control units, instruments, control devices, and other components of the apparatus and programmed to perform the routines, processes and methods described herein.

FIGS. $2A_1$, $2A_2$, $2B_1$ and $2B_2$ provide legends so that the other detailed schematics of embodiments of this disclosure can be more readily understood. Specifically, they convey the meaning and function of certain components represented symbolically in the schematics including valves, flow elements, flow meters, level instruments, pumps, motors, blowers, fans, turbines, dampers, pressure instruments, strainers/filters, temperature instruments, controls, and miscellaneous items. As used herein, the term "instruments" may refer to any component that is used to measure a physical parameter of water or steam such as flow rate, pressure and temperature. Similarly, the term "device" may refer to any component that manipulates the flow of water or steam. However, it is contemplated that either term may be interchanged with each other. Ultimately, the context of how the term is used should relay the intended meaning to the reader of this disclosure and the claims.

Turning now to FIG. 2C, a detailed schematic depicting the design of an embodiment of the feedwater supply system 110 following the direction of flow from the main feedwater pump 111 to the steam generating system 120 is given. As can be seen, the feedwater pump 111 includes a motor faceplate 202 that is in integral with the PLC and is displayed on the GUI or HMI of the control system and helps control the operation of the pump. The motor faceplate 202 includes several inputs including a hand switch 204 signal that can be placed in an off or auto position, a feedwater pump vibration high alarm signal 206 that alarms and is hardwired in series with the pump starter contactor that can shut the motor off if the pump vibrates too much, and a feedwater drip oil tank level is not low signal 208 that allows the pump to start if sufficient drip oil is present. Also, a switch 209 is hardwired in series with the pump starter contactor and sends a low level alarm to the PLC that indicates whether the feedwater pump crankcase oil level is not low. Additionally, a feedwater pump run confirmation signal 210 is sent from the pump to the motor faceplate 202 once a turn pump on signal 211 has been sent to the pump 111 and the pump begins to run. Of course, the pump can be turned off by a similar signal.

There are two inlets 212a,b shown on the schematic for the pump 111 and two outlets 214a,b but it is to be understood that this arrangement would work in a similar fashion as the single inlet and outlet shown in FIG. 1B. There are dampening devices on the pump inlet 216 and pump outlet 205 that connect to the pump via inlet 212b and outlet 214a that are commonly used in the art for dissipating vibration or pulsations made by the feed pump 111. The first outlet 214a provides feedwater to the steam generating system 120 while the second outlet 214b sends water to the flow rate control loop 113 as previously described with respect to FIG. 1C. This flow rate control loop includes a recirculation feedwater flow rate control valve 218 (analogous to valve 115 of FIG. 1C), and a valve position measuring device 222 associated with the control valve 218 and associated control device 224. Also, feedwater flow control valve demand signal device 225 that is in communication with the PLC is provided.

Immediately before the inlet 212 there is positioned an inlet feedwater pump pressure indicating instrument 226 and an associated control signal/alarm device 228 that can indicate if the feedwater inlet pump pressure is too low as this could damage the pump. Located downstream from the first outlet 214a is feedwater pump outlet pressure indicating instrument 230 as well as an associated control device 232. Located further downstream is a feedwater flow indicating device 234 and an associated control device 236 that is in communication with the PLC via a software link to send an alarm 237 if the feedwater flow rate is too low as this could cause components of the steam generating system 120 to overheat or be otherwise damaged. The alarm goes to the burner management system (BMS) as a burner run permissive condition, if the flow rate is too low then the burner is shut down. The control signal devices 232 and 236 are in communication with the feedwater recirculation control valve 218 as well as other controls associated with the delivery system 130 as will be described in more detail later for allowing control of the feedwater flow rate. The methods associated with the control of the feedwater flow rate will be elaborated upon later herein.

FIG. 2D shows a detailed schematic of the steam generating system 120. It receives water from the feedwater supply system just described and then includes a temperature indicating instrument 238 and an associated control device 240 for measuring the temperature of the water as it exits the feed pump 111 before it enters the PIP heat exchanger section 122 and for giving an alarm 240 if the temperature is too high. If the temperature exceeds the maximum operating temperature for the feed pump 111, control device 241 will communicate with the burner management system to trip the burner. The water then proceeds through the PIP heat exchanger section 122 and exits as previously described in relation to FIGS. 1A and 1B and then exits where its temperature and pressure are measured using pressure transmitting instrument 242 and temperature sensor instrument 244, that each have control devices 246, 248.

Next, the water flows through the extended surface economizer 121. A temperature indicating instrument 250 in the form of a thermocouple or resistance temperature detector measures the temperature of the flue gases exiting the extended surface economizer 121. Its associated control device 252 performs two functions. An alarm is generated via the PLC as an indication of excessive ash buildup. The second but primary function of the temperature control device 252 is as an input to the steam quality algorithm which will be elaborated upon later. The water then exits the extended surface economizer and flows back through the PIP heat exchanger as previously described. The temperature of the water as it enters and exits the PIP heat exchanger is again measured by temperature measuring instruments 254, 256 to make sure that its temperature is within acceptable parameters as it enters and exits the PIP heat exchanger respectively. If not, the associated alarm devices 258, 260 of the PLC are notified.

The water then flows through the bare tube section of the system 124 and exits toward the radiant section 126 where its pressure and temperature are measured by instruments 262, 264 respectively and monitored by their associated control devices 266, 268 respectively. If these values are outside of acceptable parameters, an alarm signal is generated from the PLC. The water then enters the radiant section 126 where it is heated even further to turn the majority of the water into steam. The temperature of the pipe/water in the radiant section is measured by a temperature measuring instrument 270 to see if its temperature exceeds a maximum value. The associated control device 272 signals and relays it to the PLC and triggers an alarm 272 if the maximum operating threshold value is exceeded. If the temperature continues to rise above the setpoint established in temperature control device 273, the burner will be stopped to prevent possible damage to the radiant section 126 of the system 120. As the steam exits the heat generating system 120, its target quality is usually in the 80 to 90 percent range where it heads toward the delivery system 130.

Focusing on the burner 128, its operation and control in relation to other inputs to the PLC will be discussed in more detail later with respect to FIG. 3A thru 3C. It should be noted that the flue gases created in the radiant section 126 travel up through the bare tube section 124 and extended surface economizer section 121 until it reaches the vent or flue found physically on top of the extended surface economizer where the oxygen content of the gases is analyzed by sensor 274. The amount of oxygen content is relayed to the PLC through the associated control device 276 if the oxygen content is too high or too low. A low oxygen alarm 275 indicates incomplete combustion and not enough air is being sent to the burner. Too much oxygen content indicates an error in the analyzer. When there is excess fuel or when not enough oxygen is being sent to the burner as required per stoichiometric predictions, small pockets of unburned fuel may collect within the furnace 126 that auto-ignite randomly which is undesirable. Accordingly, it is desirable to run the combustion with a 3-4% oxygen rich mixture. Also, as alluded to above, the stack temperature is taken by a thermocouple 250 to make sure it does not exceed a maximum value and this information is relayed to the control device 252 and the PLC.

The steam and water delivery system 130 will now be described with reference to FIG. $2E_1$, $2E_2$ and $2E_3$ where it is illustrated by another detailed schematic. Focusing for now on FIG. $2E_1$, the steam/water mixture travels to a steam separator 278 that is part of the steam quality measuring subsystem 132 that takes a portion of the water from the mixture and sends it to a sample cooler 280 where it is cooled and its conductivity is measured and compared to the conductivity of the incoming feedwater. This allows the quality of the steam/water mixture to be calculated. This is done manually on a periodic basis using equipment and methods commonly known in the art such as a conductivity measurement instrument. This actual value is then compared to a theoretical value that is calculated using an algorithm programmed into the PLC to be elaborated upon later that predicts and helps attain a desired steam quality based on measurements taken and controlled by the control system. An adjustment is then made by entering a correction coefficient into the program done manually by the user each time the steam quality is measured to correct for predictive error in the algorithm or other inefficiencies in the apparatus. This is done using a GUI (graphical user interface) or HMI (human-machine interface) such as a touchscreen as is well known in the art but other devices and methods could be used such as a keyboard, mouse, etc. A thorough discussion of this algorithm is forthcoming. It is also contemplated that this process could be automated.

The steam quality measuring subsystem 132 provides an intermittent slip stream of the main flow path and the majority of the steam/water mixture proceeds to flow toward the venting subsystem 134 (see FIGS. $2E_1$, $2E_2$ and $2E_3$) down the main steam header supply pipe 285 that includes first and second pressure safety valves 282 and 284 respectively, that vent to atmosphere if a pressure surge occurs that exceeds certain thresholds. Later, the steam/water mixture arrives at a vent pipe 286 that includes a pressure control valve 288 that can be selectively opened when desired in conjunction with the closing of other valves in the delivery system 130 in order to vent at least one of water and steam to a tank or reservoir as will be discussed in more detail later herein. There is a valve position indicating device 290 that is associated with this valve 288 as well as a valve position demand signaling device 292 as well as a control device 293 within the PLC that is in communication with device 292. Both the valve position indicating device 290 and its associated controller 291 as well as the control device 293 communicate with the PLC so that it knows when to open or close the valve and at what position the valve actually is located.

Along the main steam header pipe 285 there is a flow indicating instrument 294 (see FIG. $2E_1$) that is part of the steam injection subsystem 138 that includes an associated control device 295 that measures the flow of the steam/water mixture to make sure that it is not too high or too low and sends that signal to the PLC. After that, there is a main steam header pressure measuring device 298 (see FIG. $2E_2$) that includes an associated control device 281 that communicates with the PLC to show whether the pressure is too high or too low. At the same time, control signal device 281 is in communication via the PLC creating a valve position demand signal 283 that opens or closes the main header pressure control valve 296 (see FIG. $2E_3$), the position of which is detected and transmitted to the PLC through position indicating instrument 287 and an associated control instrument 289 (see FIG. $2E_2$). These devices and instruments also work together for opening and closing the pressure control valve 288 for the venting line when desired. This arrangement and control logic allows the valves 296, 288 to operate in tandem in a manner that will be discussed in more detail later.

Another temperature measurement instrument 251 that is part of the steam injection subsystem 138 is found along the main steam header pipe 285 that indicates through an associated control device 253 whether the temperature of the steam/water mixture is still within an acceptable high and low range. If the temperature continues to rise to a very high level, the PLC will send a signal 255 to the burner management system to turn off the burner. The last measurement device found along the main steam header pipe is pressure transmitting instrument 297 (see FIG. $2E_3$) that includes an associated control device 299 that is in communication with the PLC and feedwater recirculation flow control valve 218 as alluded to above with reference to FIG. 2C. This valve 218 and main steam pressure control valve 296 work together to modify the feedwater flow rate and injection pressure, which directly influence each other, to provide the desired pressure of the steam/water mixture to the injection well while also maintaining a consistent pressure in the steam generating system 120. This cooperation between these valves and the PLC will be discussed more thoroughly later.

Branching off the main steam header pipe 285 is the supply line 267 (see FIG. $2E_2$) that diverts part of the steam/water mixture to the bleed-off subsystem 136 for supplying auxiliary equipment with steam at a reduced pressure. A pressure control or flash valve 269 is provided that reduces the pressure by approximately 90%. Associated actual valve indicating device 207 and its associated controller 215, and valve position demand signaling device 213 as well as pressure control device 217 are provided in similar fashion as has been described for other pressure and flow control valves. Also, a steam pressure measuring instrument 219 transmits a signal to the PLC which, through an algorithm or routine, sends a signal to the pressure control device 217 to the pressure control or flash valve 269 to maintain pressure. Then a steam separator 221 (see FIG. $2E_3$) removes the water from the mixture and sends it to the feedwater preheater for the sake of conservation of energy to begin to warm up the feedwater. The remaining steam is sent to the oil burner 128 for atomizing the fuel, to the feedwater preheater to conserve energy and warm up the feedwater, and to the warm the fuel of the oil heater when heavy oil is being used.

It is to be understood that components used for the apparatus just described are often commercially available and can be interchanged with similar devices known in the art depending on the application. For example, the instruments and devices described herein are mostly pneumatically powered by a system-wide air compressor but it is contemplated that other devices powered by other methods or devices such as hydraulics, electrical or mechanical could be employed. Likewise, the control system could be altered using any devices or methods known in the art suitable for implementing various methods for startup and continuous operation as will be described later herein. For example, other control systems could be used such as mechanical linkages, computer or hard-wired digital logic systems. Similarly, wires have been used that convey a signal ranging from 4 mA to 20 mA but other systems could be chosen. When using such a signal, 4 mA corresponds to a signal for closing a device or minimizing a readout while a 20 mA signal corresponds to a signal for opening a device or for maximizing a readout and for analog applications, anything between these values is calibrated to create a proportional reading or control of a device. Of course, valve operations could be designed to operate in the opposite direction with the same control signal.

FIGS. 3A, 3B and 3C show in a segmented fashion a detailed schematic of the inputs and outputs and related control system associated with burner unit 128 that is designed to use multiple fuels including natural gas, #2 oil (diesel) and/or #6 oil (heavy oil) and/or any other gaseous or liquid fuel (best seen in FIG. 3A is a typical schematic of such a burner). For example, gas may be sent to the burner with its flow rate controlled by flow rate control valve 300 (see FIG. 3B). The flow rate may be monitored using flow transmitting instrument signal 303 conveyed to the PLC. Natural gas supply instrument 302 transmits its signal to the PLC to alarm if conditions or measurements are abnormally low or high. Both the valve and the flow measuring instrument are in communication with control device 304. If not enough gas is being sent to the ignition system, then a demand signal 306 is increased, which in turn causes the valve to open. Similarly, other fuels can be used separately or in tandem with each other and be controlled in like manner to what has just been described so that the amount of fuel, and therefore, energy might be calculated in conjunction with the air flow rate. The air flow rate is measured using a flow element 308 (see top of FIG. 3A). If more air is needed, then a control signal 310 is sent to the fan or blower 129 by the controller 312, which in turn increases the rate of rotation of the fan (see top of FIG. 3B). Likewise, the air flow could be adjusted using devices or methods known in the art suitable for this application.

An Atomizing media, such as steam that is received from the bleed-off system as has been described or compressed air is sent to the burner to mix with oil to atomize the oil and reduce its particle size to improve its combustion efficiency in the furnace (see FIG. 3C). Propane or natural gas is also supplied for creating the pilot light for the burner. Excess oil not needed by the burner is returned to the oil tank (see bottom of FIG. 3A). Likewise other methods of atomizing the liquid fuels known in the art are suitable for this application.

Also, the control system may be able to sense when the feedwater rate is increased or decreased and may adjust the burn rate accordingly. That is to say, the fuel and air rates would also being increased to compensate for the increased feedwater flow rate in an attempt to maintain the desired steam quality that is made by the steam generating system.

With reference to the architecture of the various systems that comprise various embodiments of the apparatus of this disclosure, a number of protocols, algorithms, processes, or methods may be employed for startup and normal continuous operation including those that follow. For sake of convenience and clarity for the reader, Table I is provided below that shows a description of some of the devices/signals, signal inputs/outputs and alarm annunciators as well as their associated reference numerals and I/O type for the control system. For this table, DI represents digital input, DO represents digital output, AI represents analog input and AO represents analog output.

TABLE I

| I/O Type | Ref. Numeral | Description of Device/Signal |
|---|---|---|
| DI | 228 | Feedwater Pump Inlet Pressure Low Alarm/Device |
| DI | 204 | Feedwater Pump Hand Switch In Auto |
| DI | 206 | Feedwater Pump Vibration High Alarm |
| DI | 208 | Feedwater Pump Drip Oil Tank Level Low Alarm |
| DI | 209 | Feedwater Pump Crankcase Oil Tank Level Low Alarm |
| DI | 210 | Feedwater Pump Run Confirm |
| DO | 211 | Feedwater Pump Start/Stop |
| AI | 207 | Process Steam Pressure Control Valve Position |
| AI | 219 | Process Steam Pressure |
| AI | 222 | Feedwater Flow Control Valve Position |
| AI | 230 | Feedwater Pump Outlet Pressure |
| AI | 234 | Feedwater Flow |
| AI | 238 | Feedwater Pump Outlet Temperature |
| AI | 242 | Extended Surface Economizer Feedwater Inlet Pressure |
| AI | 244 | Extended Surface Economizer Feedwater Inlet Temperature |
| AI | 250 | Stack Temperature |
| AI | 251 | Main Steam Header Temperature |
| AI | 254 | Extended Surface Economizer Feedwater Outlet Temperature |
| AI | 256 | Bare Tube Section Feedwater Inlet Temperature |
| AI | 262 | Radiant Section Feedwater Inlet Pressure |
| AI | 264 | Radiant Section Feedwater Inlet Temperature |
| AI | 270 | Radiant Section Steam Outlet Temperature |
| AI | 274 | Flue Gas Oxygen |
| AI | 287 | Main Steam Header Pressure Control Valve Position |
| AI | 290 | Main Steam Startup Valve Position |
| AI | 294 | Main Header Steam Flow |
| AI | 297 | Injection Steam Pressure |
| AO | 213 | Process Steam Pressure Control Valve Demand |
| AO | 225 | Feedwater Flow Control Valve Demand |
| AO | 283 | Main Steam Pressure Control Valve Demand |
| AO | 292 | Startup Valve Demand |

As depicted by FIG. 4 in generalized steps and sub-process steps, a startup algorithm or routine 400 may be implemented by the control system and executed to perform the following method for starting the apparatus. First, the following conditions should be satisfied before the feedwater pump 111 start command is issued and the run contact is energized. The motor trip alarm should have been reset (step 402). One of the booster pumps that provides flow to the feedwater pump should be running (step 404) which is proven if the feedwater pump inlet pressure is not too low (step 406). The hand switch of the feedwater pump should be in the auto position (step 402). Also, the feedwater pump outlet pressure must not be too high, the feedwater pump outlet temperature must not be too high (step 408), the feedwater pump vibration switch must be reset, and the feedwater pump drip oil tank level must not be too low (step 410). Also, the air instrument pressure must not be too low (step 412) or instruments must be otherwise energized. Finally, the feedwater pump crankcase oil level must not be too low (step 414). Of course, these conditions may vary depending on the selection of the pump and the overall design of the system. Accordingly, the algorithm or routine and associated method in its broadest interpretation may reduce all these conditions into a go or no go situation, that is to say, is it permissible for the feedwater pump to run (step 413). If so, then the algorithm or routine 400 or method should proceed to the next step.

At a minimum in certain embodiments, it is desirable that the downstream temperature and pressure of the water from the pump be not too high, and that the instrumentation for the apparatus be powered. For example, the valves, actuators and other devices should be supplied with enough air or hydraulic pressure, enough electricity or mechanical force, or other form of energy depending on the device to work properly. If at least minimum of these conditions is satisfied for these embodiments, then it is permissible for the pump to be energized.

Provided that it is permissible for the feedwater pump to run, a signal is sent to the feedwater pump to turn it on and the starter contact sends a signal back to the controller confirming that pump is in fact running. If this contact is not made when the run confirmation timer expires, a feedwater pump failed to start alarm is annunciated and the run contact is de-energized. If the pump inlet pressure switch opens, the feedwater pump will trip and a feedwater pump low inlet pressure alarm is annunciated. If the feedwater outlet pressure exceeds the high limit, the feedwater pump will trip and a feedwater pump outlet pressure high alarm is annunciated. If the feedwater outlet temperature exceeds the high limit, the feedwater pump will trip and a feedwater pump outlet temperature high alarm is annunciated. Any one of these alarms or warnings can lead to a shutdown of the feedwater pump after the pump has been turned on.

If the instrument air pressure (not shown in the schematics) or other powering system when other types of instruments are used is not providing the necessary energy, the feedwater pump will trip and an instrument low air pressure alarm or other similar type of alarm will be annunciated. If the pump vibration switch opens, the feedwater pump high vibration alarm will be annunciated and since the switch is also hardwired in series with the pump starter contactor, the feedwater pump will trip. Likewise, if the feedwater pump crankcase oil level switch opens, the feedwater pump low crankcase oil level alarm will be annunciated and since the switch is also hardwired in series with the pump starter contactor, the feedwater pump will trip. Again, any one of these alarms or warnings can lead to a shutdown of the feedwater pump after it has been turned on.

If the feedwater pump drip oil tank level switch opens, a feedwater pump drip oil tank low level alarm will be annunciated and a one hour timer will start. In order to stop the running of this timer, the operator needs to reset the alarm by pushing the reset button after refilling the drip oil tank. If the feedwater pump drip oil tank low level switch stays open for more than one continuous hour, the feedwater pump will trip. Of course, this can occur at any time during the operation of the pump.

Assuming that the feedwater pump is running, then the start routine 400, method or associated algorithm proceeds to the next step as follows. The startup valve 288 is opened an appropriate amount to vent steam and water directly from the main steam header pipe 285 to the vent tank or reservoir (step 415) until it has been determined that the steam/water mixture is suitable (step 416) to be sent toward the injection well or other desired destination (step 418). At the same time the main header pressure control valve 296 is closed an appropriate amount or entirely until the desired parameters have been achieved. This can all be done dependent on parameters input by a user or that were previously programmed into the controller. Of course, any of these steps of this method or any other discussed herein may in certain cases be performed in a different order or may be omitted depending on the application and design of the apparatus. Consequently, the flowchart in FIG. 4 is depicted in broad steps and should not be construed as the sole embodiment of this disclosure. Additionally, more steps could be added to this routine or method or any other routine or method discussed herein.

Turning now to FIG. 5A, another method or routine 500 that can be implemented by the control system and executed during normal operation includes the following steps. The injection pressure at the injection well or other desired location is determined to be within acceptable parameters (step 502). If not, then the feedwater flow rate is adjusted (step 504) as well as the burn rate (step 506) of the burner of the steam generating system. Then, it is determined whether the feedwater flow rate and pump discharge pressure are within acceptable parameters (step 508). If not, then the feedwater flow rate is adjusted (step 510). This method was alluded to above with respect to the maintenance of the injection pressure using the recirculation feedwater flow rate control valve 218.

Referring to FIG. 5B, sub-processes or subroutines and their steps are shown for determining whether the injection pressure is within acceptable parameters, for adjusting the feedwater flow rate and for adjusting the burn rate. In one embodiment, a desired setting for the injection steam pressure is placed into the computer such as by the user via an input device or preprogrammed into the PLC. The injection steam pressure is then measured. If the injection steam pressure is too low as compared to the desired setting (step 512), then the recirculation feedwater flow rate control valve is closed an appropriate amount (step 514). If the injection steam pressure is too high as compared to the desired setting (step 516), then the recirculation feedwater flow rate control valve is opened an appropriate amount (step 518). This can be automated using the PLC since all the necessary components are communicating with the PLC and therefore with each other. This can be considered the first control loop 520 for maintaining the desired main steam header pressure. Naturally, steps 522 and 524 require that the burn rate be raised or lowered respectively to match the increase or decrease in the flow rate in an effort to maintain the desired steam quality.

There can also be a secondary control loop 526 that is also depicted by FIG. 5B based on the feedwater flow rate. It would comprise the following steps: measuring the feedwater flow rate, inputting a maximum value for the flow rate into the control system, which may be done in any manner including manually or by programming, and comparing the feedwater flow rate to the maximum value for the flow rate. If the feedwater flow rate is above the threshold value (step 528), then the second control loop takes precedence over the first control loop and the flow rate is decreased (step 530) even if the desired injection steam pressure has not been reached. On the other hand, if the flow rate is too low (step 532), then the flow rate may be increased (step 534) as long as the pump discharge pressure is not too high (step 533).

In certain embodiments as shown by FIG. 5C, either the controller linked to the feedwater flow rate or to the injection steam pressure controller can be placed in manual or automatic mode. This yields four separate scenarios with the typical scenario being the one where both controls are placed in automatic mode (step 536).

This first scenario allows the injection steam pressure controller to control the feedwater flow rate until the desired pressure has been reached. This may involve the steps of inputting the desired injection pressure range into the control system (step 538). Then, the injection pressure and feedwater flow rate are measured (step 540). This continues until the feedwater flow rate or the injection pressure are not within desired ranges (step 542). Then, the recirculation feedwater flow rate control valve is opened or closed as necessary to obtain the desired injection pressure range (step 544). The output of the feedwater flow rate controller is at and remains at 0% until the flow rate approaches the high flow limit, such as when it exceeds the design conditions of the steam generator, at which time its output is greater than the output of the injection steam pressure controller and controls the recirculation feedwater flow rate. The high feedwater flow rate limit is sometimes automatically set when the injection steam pressure controller is placed into automatic mode to avoid an operator forgetting to set the appropriate limit. Typically, these control loops can only be put into automatic if the feedwater pump is running. If the feedwater pump stops for any reason including those related to the conditions necessary to start the pump discussed with reference to FIG. 4 above, both the feedwater flow rate controller and injection steam pressure controller are placed into manual mode and the output is placed to 100% so at least a minimal amount of water flows to the steam generating system helping to keep its components from overheating. It is to be understood that a setpoint for any value whether it be flow rate, pressure or temperature disclosed herein may include a range or single setpoint so the term range or setpoint should be considered equivalents of each other.

As mentioned previously when looking at FIG. 2C, a position transmitter 222 provides position feedback from the feedwater flow rate control valve 218 (see step 546 of FIG. 5C). If the actual position deviates more than 5% from the valve position demand signal 225 (step 548), a feedwater flow rate control valve position deviation alarm is annunciated to alert that there may be a problem with the valve (step 550). These steps of measuring a valve's position, comparing it to a desired position, and annunciating an alarm if the deviation is too great may be used in conjunction with any valve that includes the appropriate instruments and controls.

In the second scenario, both the feedwater flow rate controller and the injection steam pressure controller are both placed in manual mode so they need to track each other. The output buttons on the injection steam pressure controller are not visible to the operator when both controllers are in manual mode. Consequently, the operator only has access to manipulate the output of the feedwater flow rate controller (shown as 236 in FIG. 2C) and the logic of the PLC tracks this and matches it on the injection steam pressure controller (shown as pressure controller 299 in FIG. 2E$_3$).

In the third scenario, the feedwater flow rate controller is in automatic mode and the injection steam pressure controller is placed in manual mode. In such a case, the recirculation feedwater flow rate control valve is always opened or closed to the higher of either controller output. If the output of the injection steam pressure controller is set to 100%, then the output of the feedwater flow rate controller has no effect, since the control valve will always stay at 100%. In order for the feedwater flow rate controller to exclusively control the valve when it is in automatic mode, the setting for the injection steam pressure controller has to be 0%.

In the fourth scenario, the feedwater flow rate controller is put into manual mode and the injection steam pressure controller is placed into automatic mode. The result is the same as the second scenario except that the output of the feedwater flow rate controller must be set to 0% in order for the injection steam pressure controller to be exclusively in control.

While scenarios three and four are used from time to time to manually control the steam injection pressure or feedwater flow rate respectively, the first scenario is the one typically used and involves placing both the feedwater flow rate controller and the injection steam pressure controller into automatic mode. The second scenario is discouraged as it does not take advantage of the control system and its logic.

FIG. 6 depicts the steps of another routine 600 or method that can be implemented and executed by the control system. This routine 600 is well suited once the startup routine has been accomplished and normal operation has ensued. Once the steam/water mixture is determined to be of suitable quality, the main header pressure control valve 296 is opened and the startup valve 288 is closed an appropriate amount to maintain the main steam header pressure at an operator selected or preprogrammed level. Also, excess steam pressure that may arise during some sort of event, excursion or surge can be vented using the vent or startup valve 288.

Specifically, the main steam header pressure 298 is controlled by a backpressure control valve 296 in the main steam line 285 (see FIGS. 2E$_2$ and 2E$_3$). First, it is determined whether the pressure in the main steam header pipe or line is within acceptable parameters (step 612 in FIG. 6). A possible sub-process or subroutine for this may include the following steps. A desired pressure is input into the main steam header pressure controller 287 (step 604 in FIG. 6) by any method including manually or by programming. This controller can only be put into automatic mode (step 602) if the feedwater pump 111 is running and the burner 128 is released for modulation, that is to say, it is in normal operation mode. The pressure is then measured and compared to the desired value (step 614).

Referring back to the main process, if the measured pressure is greater than the desired value, then the steam and/or water mixture is sent to the venting reservoir (step 616). If either the feedwater pump stops (step 606) or the burner is shut off (step 608), this controller is automatically switched to manual (step 610) and the output is pulsed to zero and backpressure control valve 296 closes so that some pressure is maintained within the steam generation system. Once more, the same conditions that have been discussed as necessary to start the feedwater pump could also cause the pump to stop if they are not satisfied. Also, a position transmitter 287 provides position feedback from the main steam header pressure control valve 296. If the actual valve position deviates more than 5% from the valve position demand signal 283, a main steam header pressure control valve position deviation alarm is annunciated. Lastly, the main steam header pipe may be provided with pressure safety valves 282, 284. This method may also include the step of determining whether the pressure in the main steam header pipe is greater than the designed release pressure of one of the safety valves (step 618). If so, then one of the pressure safety valves opens. It should be noted that this may be done without any signal from the control system as such valves are usually constructed with a mechanical spring that keeps the valve closed until a setpoint steam pressure overcomes the spring pressure opening the valve (step 620).

Yet another routine, algorithm or associated method that can be implemented by the control system during normal operation comprises the following steps. First, the pressure setting for the vent pressure control valve or startup valve 288 is set at a threshold value by any suitable method including manually or via a program so that its value is slightly higher than main steam header pressure controller 281 setting. If the pressure exceeds this threshold value, then the vent pressure control valve 288 opens up an appropriate amount to allow excess steam pressure to escape to the venting reservoir. Thus, the valve provides both the functions of an excess steam pressure relief valve when there is a surge or excursion in the main steam header pressure or injection steam pressure during startup and normal operation. In an embodiment, the controller associated with the startup valve 288 is automatically placed in automatic mode by the PLC logic when the feedwater pump is started. If the feedwater pump stops, then this controller 293 is automatically switched to manual and the output is pulsed to zero and the startup valve 288 is closed as it is desired to maintain some pressure and water in the steam generation system to help prevent overheating. A position transmitter 290 tells the control system the position of the valve 288 and if the actual position deviates more than 5% from the valve position demand signal 292, a startup or vent valve position deviation alarm is annunciated.

Turning attention now to the bleed-off subsystem, a process steam control valve 269 is used to reduce the steam pressure from the main steam header pressure to a suitable pressure for the process steam that is sent to the fuel oil heater, feedwater heater, burner atomizing steam and soot blower (not shown in the figures). The following method and associated algorithm may be employed during normal operation. First, a desired pressure is placed in the process steam pressure controller 217. The pressure is then measured using pressure measuring device 219. If the pressure is not within acceptable parameters, then the valve is opened or closed as needed to place the pressure in the desired range. In an embodiment, this controller can only be placed in automatic mode if the feedwater pump is running and the burner has been released for modulation, that is to say, it has been cleared by the control system for normal operation. If the feedwater pump stops or the burner is shut off, this controller is automatically switched to manual and the output is pulsed to zero, and the valve is closed, as it is desired to maintain some water pressure in the steam generation and delivery systems. A valve position transmitter 207 provides position feedback from the process steam pressure control valve 269. If the actual valve position deviates more than 5% from the valve position demand signal 213, a process steam pressure control valve position deviation alarm is annunciated.

Yet another routine 700 (see FIG. 7A), algorithm or method that can be implemented by the control system provides the following process for adjusting the burner firing rate to achieve a desired steam quality being sent to the injection well or other desired destination from the steam generating system. First, the temperature of the water supplied by the feedwater system to the steam generation system as well as its flow rate and enthalpy are determined (step 714) by any device or method known in the art or that will be devised in the art. This step may be achieved using sub-steps of a sub-process or subroutine including the following. If the feedwater temperature signal quality input to the control system is within acceptable parameters (step 702), then the feedwater enthalpy is calculated by subtracting a value of thirty-two from the measured temperature in degrees F. to get the feedwater enthalpy in BTU/lb (step 704). If the temperature's electronic signal quality is bad, then the temperature is assumed to be about 200 degrees F. and the feedwater enthalpy is estimated to be 168 BTU/lb (step 706). It is contemplated that the enthalpy of the water could be estimated some other way such as using a table since the system is capable of measuring the temperature and pressure of the water.

Second, as best shown by FIGS. 7A and 7B, the algorithm computes or estimates the target steam enthalpy (step 710) based on the operator set target percent value for the steam quality that has been entered into the control system using an input device (step 708) such as a HMI and the current main steam header pressure instrument 298 signal using the following equation: Target Steam Enthalpy=(Target Steam Quality Percent/100)*(Current Enthalpy of the Steam Vapor−Current Enthalpy of the Steam Liquid))+Current Enthalpy of the Steam Liquid (step 716 of FIG. 7B) where steam quality is initially expressed as a percent. The current steam header vapor and liquid enthalpies associated with the main steam header pressure are retrieved from look-up tables that are based on ASME steam tables and are stored in a database. In one embodiment, the tables cover a pressure range from 0 to 1800 psig with an enthalpy value for every 100 psi increment (step 718 of FIG. 7B). The program may determine if the pressure is located between those listed in the table (step 720 of FIG. 7B) and may automatically interpolate for pressures found between these 100 psi listed increments (step 722). It is to be understood that similar programs known in the art may be used to determine the steam vapor and steam liquid enthalpies. The pressure of the steam/water mixture is measured as it exits the steam generation system in a manner that has already been described. It is contemplated that the desired steam quality could be set by any known method or device known in the art or that will be devised in the art (step 712 of FIG. 7A) such as by preprogramming without the need of a user to input a value into the control system.

The next step (step 724 of FIG. 7A) includes calculating the amount of heat that is required to be added to each pound of feedwater in order to achieve the desired steam quality. This may be accomplished by subtracting the feedwater enthalpy from the target steam enthalpy, both of which have been calculated as discussed above. This may be represented by the following equation: Heat Required=Target Steam Enthalpy−Feedwater Enthalpy.

However, the amount of heat that must be generated and put into the water by the steam generating system is affected by the efficiency of the steam generating system, especially that of the boiler which includes the radiant section, bare tube section and the extended surface economizer section. The boiler efficiency can be estimated as follows as best seen in FIG. 7C. First, the flue gas oxygen level signal and content are measured as has been previously described to determine if it is within an acceptable range (step 726). In one embodiment, the transmitted signal to the control system from 274 will be between 3.8 and 21.0 mA. If it is within this range, then the actual corresponding oxygen content is used in the calculation involving the boiler efficiency (step 728). If it is outside this range, then the flue gas oxygen content is assumed to be 3% (step 730). Similarly, the stack temperature signal is measured, and if its signal is within acceptable parameters (step 732), the actual temperature provided by the thermocouple or other measuring instrument is used in the calculation (step 734). In one embodiment, this range is anything that falls within these signal limits. If the measured temperature is outside the permissible range, then a temperature of 480 degrees F. is assumed (step 736). Also, the type of fuel burned in the burner is considered (step 738). If natural gas is used as fuel, then an equation is derived from a matrix of efficiency numbers obtained from running a boiler heat balance program for various flue gas oxygen values and stack temperatures (step 740). The calculation may be made using the equation as follows: Boiler Efficiency=Boiler Specific Factor+(20.95/(20.95−Measured Flue Gas Oxygen Percent)* 0.02153*(350−Measured Stack Temperature))−Radiation Loss. (See step 742).

Specifically, the equation given above is determined by fitting a curve to experimental data where the specific type of unit and its inherent inefficiencies are taken into account to develop the Boiler Specific Factor above as well as the effects that the Flue Gas Oxygen Content and the Stack Temperature have on the unit's efficiency while using natural gas. In one embodiment, the Radiation Loss can be assumed to be 1% and is stored in the database. Alternatively, if #6 oil is used, then the equation is adjusted as follows: Boiler Efficiency=Boiler Specific Factor+(20.95/ (20.95−Measured Flue Gas Oxygen Percent)*0.02117* (350−Measured Stack Temperature))−Radiation Loss. If #2 oil is chosen to be burned, then 0.61% is subtracted from this calculation to get the Boiler Efficiency for #2 oil.

Next, it is determined if the calculated efficiency is within the range of 60 to 95% (step 744). If the calculated boiler efficiency number is greater than 95%, then the algorithm assumes that the boiler efficiency unit is 95%. If the calculated boiler efficiency number is less than 60%, then the algorithm assumes that the boiler efficiency is 60% (step 746). Otherwise, the boiler efficiency is set to the calculated value found between 60 and 95% (step 748).

Once the boiler efficiency has been determined as well as the required heat input, then the Specific Gross Heat Input per pound of feedwater can be calculated by dividing the required heat input (step 724) by the appropriate boiler efficiency (step 750). This step can be represented by the following equation: Specific Gross Heat Input=Heat Required/Boiler Efficiency.

Turning back to FIG. 7A, the Gross Heat Input Rate is calculated in thousands of BTU/hr by multiplying the specific gross heat input just discussed by the measured feedwater flow rate (step 752). This step is represented by the following equation: Gross Heat Input Rate=2,205*Feedwater Flow Rate*Specific Gross Heat Input/1000 where the Feedwater Flow Rate is calculated using mt/h (metric tons per hour) and the conversion factor is built into the equation.

Once the Gross Heat Input Rate is determined, then an Adjusted Gross Heat Input Rate needs to be calculated depending on which fuel is being used in order to express in percent what portion of the burner heat input should be used (see FIG. 7D). If natural gas is being used (step 756), then a higher heating value is used (often provided by the operator through the input device such as a HMI) as well as a Natural Gas Load Factor that converts to the percent burner load that is stored in the database. The following equation can be used: Adjusted Gross Heat Input Rate=1000*Gross Heat Input Rate/Gas Higher Heating Value *Natural Gas Load Factor. The Natural Gas Load Factor is stored in a database and converts from SCFH (standard cubic feet per hour) to a percent (dimensionless number) of the burner load (see step 758).

Similarly, if #2 oil is used (step 760), the Adjusted Gross Heat Input Rate=1000/60* Gross Heat Input Rate/#2 Oil Higher Heating Value*#2 Oil Load Factor where this factor is stored in a database and converts from gpm to a percent of the burner load (dimensionless number) (see step 762). This factor is often fixed at 30.92 (step 764).

Finally, a similar step can be used when #6 oil is being used (step 766). In such a case, the following equation is used: Adjusted Gross Heat Input Rate=1000/60*Gross Heat Input Rate/#6 Oil Higher Heating Value*#6 Oil Load Factor where this factor is stored in a database and converts gpm to a percent of the burner load (step 768). This factor is often fixed at 32.26 (step 770).

Other gaseous or liquid fuel can be fired in the burner. Similar calculations and programming can be done.

Once the Adjusted Gross Heat Input Rate is determined, an additional factor may be multiplied to get the desired percent burner load. Once known, the PLC may automatically adjust the firing rate (step 754 of FIG. 7A) until the stack temperature and flue gas oxygen content, (and as a result the calculated boiler efficiency) change to match the required burner heat input necessary to match the desired steam quality. As mentioned earlier, the actual sampled steam quality may be compared to the predicted or desired steam quality. Any difference can be used to create a correction factor to compensate for inefficiencies in the system and error in the algorithm. So, if it is predicted that the steam quality would be 90% but it is in fact 88%, then a correction factor can be entered in the control system for adjusting for this 2% error. This would increase the burn rate by an appropriate amount to obtain the desired 90% steam quality.

In addition, the control system may use the measured steam flow in main steam header pipe to estimate what the current quality of the steam is. During startup, the feedwater flow rate is measured and the steam is sampled to determine its quality and a curve is generated throughout the operating range plotting pressure differential across the steam flow element versus quality as measured. From this curve, an estimated steam quality is displayed on the GUI or HMI and allows the operator to have an estimation of whether the steam quality is within desired parameters. If there is a difference between the estimate and actual tested steam quality, then an adjustment may be made to the burn rate. As mentioned previously, a correction coefficient can be entered into the control system to help correct for predictive error with respect to this algorithm so that it is more accurate and adjust the burner rate as needed. This error may be a result of or related to energy losses within the system and is typical with such systems. Nevertheless, it is recommended that the operator periodically check the actual steam quality using quantitative steam quality measuring instruments. This process could also be automated so that the algorithm self corrects itself on regular intervals.

Also, this process may be changed depending on the amount of accuracy needed for a particular application. Therefore, one or more of the variables just described may be omitted or substituted for or an additional variable may even be added depending on the situation. It is contemplated that this algorithm and associated process could be thus varied as long as some sort of model is used that takes into consideration the heat balance of the inputs and outputs of the steam generating system. Furthermore, the flow rates of the fuels and air may be linked so that their individual control is rendered unnecessary. For example, a mechanical control may link the fuel flow rate to the air flow rate such as the use of linkages or this could be done electronically.

The GUI or HMI of the control system may provide graphical information on the following process parameters including, the radiant section tube metal temperature 270, the main steam header temperature 251, feedwater pump outlet pressure 230, feedwater pump outlet temperature 238, extended surface economizer feedwater inlet pressure 242, extended surface economizer feedwater inlet temperature 244, extended surface economizer feedwater outlet temperature 254, bare tube section feedwater inlet temperature 256, radiant section feedwater inlet pressure 262, radiant section feedwater inlet temperature 264, and stack temperature 250 However, it is contemplated that more or less parameters could be displayed and/or available for input by a user through the GUI or HMI as desired depending on the application.

Specifically, a control system that is used with the apparatus to implement any of the methods discussed herein may include an input device that may include any number of devices or methods currently used or that will be devised in the art such as a keyboard, a mouse, a touchscreen, voice recognition, etc. Likewise, a number of output devices may be used that includes those currently used or that will be devised in the art such as a display screen, flashing lights or other visual displays or cues, audible alarms, etc. Furthermore, various control systems may be employed including a PLC, a distributed control system (DCS), a gate array logic system, a mechanical system including those that use mechanical linkages, a hard wired logic system, a microprocessor, a microcontroller, a PC that includes customized software that is configured to execute an algorithm and/or associated method, etc. It is further contemplated that any of the routines, algorithms, methods or processes described herein may be accomplished absent a formal control system such as may be the case when one or more operators are acting in concert. For any routine, process or method disclosed herein, the algorithm, processor-executable code or instructions may be stored in the PLC or in the memory of the control system for execution on the PLC or the processor to perform the operation, routine, process or method. Furthermore, the display language can be English or any other desired language.

In an embodiment of the apparatus that has just been described, it has been possible to optimize the quality of the steam with little variance, allowing more heat to be effectively pumped into an injection well, raising the number of units of oil produced from an oil well per unit heat put into a steam injection well. Put into other terms, more oil is ultimately produced for the money invested in making the steam and water mixture. In one embodiment, the feedwater supply coming into the feedwater pump as shown in FIG. 2C satisfies the following conditions: the minimum pump inlet pressure is 50 psig, the maximum inlet pressure is 150 psig, the minimum inlet temperature is 60 degrees F., the desired or normal temperature is 190 degrees F., the maximum inlet temperature is 212 degrees F., minimum flow rate is 16 gallons per minute, the desired or normal flow rate is 48 gallons per minute and the maximum flow rate is 57 gallons per minute. The feedwater pump motor may be made by TECO WESTINGHOUSE and have the following specifications: one hundred horsepower, 480 VAC with three phase at 60 Hz, 1200 RPM and it may be totally enclosed and fan cooled. The pump itself may be made by NATIONAL OILWELL under model #1100-3M and it may include the following specifications: a design or preferred allowable pressure output of 1742 psig, a maximum allowable pressure output of 2295 psig, a output temperature of 200 degrees F., a design or preferred allowable output flow rate of 48 gallons per minute and a maximum allowable output flow rate of 57 gallons per minute.

Looking at the steam generation system of FIG. 2D, the steam generator is cable of producing a heat output of 25.0 MMBTU per hour, includes a design pressure of 1760 psig and is designed, fabricated and stamped in accordance with ASME Boiler and Pressure Vessel Code Section I, Latest Edition.

Finally, some of the specifications for the equipment used in an embodiment of the delivery system such as shown by FIG. 2E will be discussed. The steam separator that is used in conjunction with the bleed-off subsystem may be made by SPIRAX SARCO under model #4 inch SC4 Special. It may be made using SA-106 GR. B steel, maximum allowable working conditions of 300 psig and 650 degrees F., and the associated inlet and outlet connections are made using 4 inch Class 300 RF flanges. A separate steam separator may be used in conjunction with the steam quality measuring subsystem that is installed in or as a side stream of the main steam header supply pipe. A device known in the art as a sample cooler is used to cool the steam sample to enable steam sample analysis. The steam quality measuring subsystem may be supplied with a shell design pressure of 285 psig, a cooling water design flow rate of 5 gallons per minute, and a stainless steel coil design pressure of 3500 psig.

The outputs from the delivery system are as follows: the normal injection pressure to a steam injection well is 1500 psig, the maximum desirable design pressure is 1760 psig, the normal temperature is 598 degrees F., the maximum desirable design temperature is 619 degrees F., the normal flow rate is 24,000 lb per hour, the maximum allowable flow rate is 24,314 lb per hour and the desired steam quality may range from 0 to 90% but is in fact often within 80-90%. The output to the blowdown tank or venting reservoir includes a design pressure of 300 psig, a design temperature of 619 degrees F., and a design flow rate of 24,000 lb per hour. The output of condensed water to the feedwater heater includes a design pressure of 250 psig, design temperature of 406 degrees F., and a design flow rate of 2,100 lbs per hour. The output of steam to the fuel oil heater includes a design pressure of 150 psig, a design temperature of 375 degrees F., and a design flow rate of 200 lb per hour. The output of steam to the feedwater heater includes a design pressure of 150 psig, a design temperature of 375 degrees F., and a design flow rate of 3,040 lb per hour. Lastly, the output of atomizing steam to the oil burner includes a design pressure of 150 psig, a design temperature of 375 degrees F., and a design flow rate of 200 lb per hour.

The control system and the present disclose of certain embodiments are not to be construed to any system, inputs, or outputs or values disclosed herein but is suitable for many different combinations of equipment and for various design parameters, operating conditions and specifications. Thus, the claims should not be limited to any specific embodiment disclosed herein.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. The logical steps, functions or operations described herein as part of a routine, process, or method may be implemented (1) as a sequence of processor-implemented acts, software modules or portions of code running on the PLC or other processor of the control system, or other computing system and/or (2) as interconnected machine logic circuits or circuit modules within the apparatus 100 and associated control system(s). The implementation is a matter of choice dependent on the performance and other requirements of the system. Alternate implementations are included in which steps, operations or functions may not be included or executed at all, may be executed out of order from that shown or discussed, including substantially concurrently or in reverse order, depending on the functionality involved, as would be understood by those reasonably skilled in the art of the present disclosure.

Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A method comprising:
   determining a feedwater enthalpy and a feedwater flow rate by at least one device in a steam generation and supply apparatus configured to extract oil from a formation, the apparatus comprising a feedwater supply system and a steam generation system;
   setting, in a control system of the apparatus, a desired steam quality of at least one of water and steam supplied by the steam generation system;
   estimating, by at least one other device in the apparatus, a target steam enthalpy of the at least one of water and steam supplied by the steam generation system; and
   automatically adjusting, by a programmable controller of the apparatus, a firing rate of a burner configured to supply heat to a boiler in the steam generation system, the automatic adjusting executed responsive to a determination of a heat input rate based at least partially upon the target steam enthalpy;
   wherein automatically adjusting the firing rate of the burner maintains the at least one of water and steam supplied by the steam generation system at the desired steam quality, allowing more heat to be pumped into an injection well and raising a number of units of oil produced from an oil well per unit heat put into a steam injection well, as compared to oil extraction systems lacking capability to automatically adjust a burner firing rate.

2. The method of claim 1, wherein the method further comprises the steps of:
   determining a pressure of the at least one of water and steam supplied by the steam generation system, wherein estimating the enthalpy of the desired steam quality of at least one of water and steam comprises determining the current enthalpies of vapor and liquid of at least one of water and steam; and
   looking up values of the current enthalpies of vapor and liquid from a table that comprises enthalpy values for vapor and liquid listed by pressure.

3. The method of claim 2, which further comprises the step of interpolating values of enthalpies for vapor and liquid at pressures found between those listed in a table.

4. The method of claim 2, wherein estimating the enthalpy of the desired steam quality of at least one of water and steam further comprises the steps of multiplying the desired steam quality in fraction form by a difference of the current enthalpies of vapor and liquid and adding a product of that calculation to the current enthalpy of liquid being generated by the steam generation system.

5. The method of claim 1, wherein the heat input rate is based at least partially upon a determination of a required amount of heat, the required amount of heat defined as heat needed to be put into feedwater to achieve the desired steam quality, the required amount of heat determined by subtracting the feedwater enthalpy from the target steam enthalpy.

6. The method of claim 5, which further comprises the step of multiplying, by the feedwater flow rate, a quotient of the required amount of heat divided by boiler efficiency to obtain an amount of heat per unit time necessary to achieve the desired steam quality.

7. The method of claim 1, wherein the boiler comprises a flue that comprises an instrument for measuring how much oxygen is present in a flue gas in the flue, and wherein the method further comprises the step of determining whether an oxygen content of the flue gas is within an acceptable range.

8. The method of claim 7, wherein the acceptable range for the oxygen content of the flue gas is between 1.5% and 21%, and wherein the method further comprises assuming a value of 3% if the oxygen content is outside of the range of 1.5% and 21%.

9. The method of claim 1, wherein the boiler comprises a thermocouple for measuring a stack temperature of the boiler, and wherein the method further comprises the step of determining whether the stack temperature is within acceptable parameters.

10. The method of claim 9, wherein the acceptable parameters include a high limit of 550 degrees F, and wherein the method further comprises the step of assuming that the stack temperature is 480 degrees F when the stack temperature measures above 480 degrees F.

11. The method of claim 9, which further comprises the step of calculating a boiler efficiency based on one of the stack temperature and oxygen content of the flue gas.

12. The method of claim 11, wherein the calculated boiler efficiency is at least partially based on an equation derived experimentally.

13. The method of claim 11, wherein calculating the boiler efficiency comprises adjusting the calculation depending on what fuel is used in the burner.

14. The method of claim 11, wherein the calculated boiler efficiency is used to determine a heat input needed to create the steam having a desired quality except if the calculated boiler efficiency is outside a prescribed range.

15. The method of claim 1, wherein the apparatus comprises a control system comprising memory and an input device, the memory having a routine for implementing the method, and wherein setting the desired steam quality comprises inputting the desired steam quality into the control system via the input device.

16. The method of claim 1, wherein determining the feedwater enthalpy comprises determining a temperature of feedwater.

17. A method comprising the steps of:
determining a feedwater enthalpy and a feedwater flow rate by at least one device in a steam generation and supply apparatus configured to extract oil from a formation, the apparatus comprising a feedwater supply system and a steam generation system;
determining, by at least one other device in the apparatus, a pressure of at least one of water and steam supplied by the steam generation system;
setting, in a control system of the apparatus, a desired steam quality of the at least one of water and steam supplied by the steam generation system;
estimating, by at least one other device in the apparatus, a target steam enthalpy of the at least one of water and steam supplied by the steam generation system by
determining current enthalpies of vapor and liquid of the at least one of water and steam,
looking up values of the current enthalpies of the vapor and liquid from a table that comprises enthalpy values for vapor and liquid listed by pressure, and
multiplying the desired steam quality in fraction form by a difference of the current enthalpies of the vapor and liquid and adding a product of that calculation to the current enthalpy of liquid being generated by the steam generation system; and
automatically adjusting, by a programmable controller of the apparatus, a firing rate of a burner configured to supply heat to a boiler in the steam generation system, the automatic adjusting executed responsive to a determination of a heat input rate based at least partially upon the target steam enthalpy;
wherein automatically adjusting the firing rate of the burner maintains the at least one of water and steam supplied by the steam generation system at the desired steam quality, allowing more heat to be pumped into an injection well and raising a number of units of oil produced from an oil well per unit heat put into the injection well, as compared to oil extraction systems lacking capability to automatically adjust a burner firing rate.

18. A method comprising the steps of:
determining a feedwater enthalpy and a feedwater flow rate by at least one device in a steam generation and supply apparatus configured to extract oil from a formation, the apparatus comprising a feedwater supply system and a steam generation system;
setting, in a control system of the apparatus, a desired steam quality of at least one of water and steam supplied by the steam generation system;
estimating, by at least one other device in the apparatus, a target steam enthalpy of the at least one of water and steam supplied by the steam generation system;
automatically adjusting, by a programmable controller of the apparatus, a firing rate of a burner configured to supply heat to a boiler in the steam generation system, the automatic adjusting executed responsive to a determination of a heat input rate based at least partially upon the target steam enthalpy;
wherein the boiler comprises a flue that comprises an instrument for measuring how much oxygen is present in a flue gas in the flue;
determining whether an oxygen content of the flue gas is within an acceptable range defined between 1.5% and 25%; and
assuming a value of 3% if the oxygen content is outside of the range of 1.5% and 25%;
wherein automatically adjusting the firing rate of the burner maintains the at least one of water and steam supplied by the steam generation system at the desired steam quality, allowing more heat to be pumped into an injection well and raising a number of units of oil produced from an oil well per unit heat put into the injection well, as compared to oil extraction systems lacking capability to automatically adjust a burner firing rate.

19. A method comprising the steps of:
determining a feedwater enthalpy and a feedwater flow rate by at least one device in a steam generation and supply apparatus configured to extract oil from a formation, the apparatus comprising a feedwater supply system and a steam generation system;
setting, in a control system of the apparatus, a desired steam quality of at least one of water and steam supplied by the steam generation system;
estimating, by at least one other device in the apparatus, a target steam enthalpy of the at least one of water and steam supplied by the steam generation system;
automatically adjusting, by a programmable controller of the apparatus, a firing rate of a burner configured to supply heat to a boiler in the steam generation system, the automatic adjusting executed responsive to a determination of a heat input rate based at least partially upon the target steam enthalpy;
wherein the boiler comprises
a flue that comprises an instrument for measuring how much oxygen is present in a flue gas in the flue, and
a thermocouple for measuring a stack temperature of the boiler;
determining whether an oxygen content of the flue gas is within an acceptable range;
determining whether the stack temperature is within acceptable parameters defined by a high limit of 550 degrees F; and
assuming that the stack temperature is 480 degrees F when the stack temperature measures above 480 degrees F;
wherein automatically adjusting the firing rate of the burner maintains the at least one of water and steam supplied by the steam generation system at the desired steam quality, allowing more heat to be pumped into an injection well and raising a number of units of oil produced from an oil well per unit heat put into the injection well, as compared to oil extraction systems lacking capability to automatically adjust a burner firing rate.

* * * * *